US010829528B2

(12) United States Patent
De Wit et al.

(10) Patent No.: US 10,829,528 B2
(45) Date of Patent: Nov. 10, 2020

(54) THERAPEUTIC AGENTS FOR NEUROLOGICAL AND PSYCHIATRIC DISORDERS

(71) Applicants: VIB VZW, Ghent (BE); KATHOLIEKE UNIVERSITEIT LEUVEN, K.U.LEUVEN R&D, Leuven (BE)

(72) Inventors: Joris De Wit, Kessel-Lo (BE); Heather Rice, Leuven (BE); Bart De Strooper, Leuven (BE)

(73) Assignees: VIB VZW, Ghent (BE); Katholieke Universiteit Leuven, K.U.Leuven R&D, Leuven (BE)

( * ) Notice: Subject to any disclaimer, the term of this patent is extended or adjusted under 35 U.S.C. 154(b) by 0 days.

(21) Appl. No.: 16/318,480

(22) PCT Filed: Jul. 14, 2017

(86) PCT No.: PCT/EP2017/067859
§ 371 (c)(1),
(2) Date: Jan. 17, 2019

(87) PCT Pub. No.: WO2018/015296
PCT Pub. Date: Jan. 25, 2018

(65) Prior Publication Data
US 2019/0225662 A1  Jul. 25, 2019

(30) Foreign Application Priority Data
Jul. 20, 2016 (EP) ..................................... 16180433

(51) Int. Cl.
G01N 33/566 (2006.01)
G01N 33/50 (2006.01)
C07K 14/00 (2006.01)
C07K 14/47 (2006.01)
A61K 38/00 (2006.01)

(52) U.S. Cl.
CPC .......... *C07K 14/4711* (2013.01); *C07K 14/00* (2013.01); *G01N 33/5008* (2013.01); *G01N 33/566* (2013.01); *A61K 38/00* (2013.01); *G01N 2500/02* (2013.01); *G01N 2500/04* (2013.01)

(58) Field of Classification Search
CPC .. C07K 14/00; G01N 33/5008; G01N 33/566; G01N 2500/02; G01N 2500/04; A61K 38/00
See application file for complete search history.

(56) References Cited

U.S. PATENT DOCUMENTS

2007/0083334 A1* 4/2007 Mintz .................... G16B 40/00
702/19
2009/0317842 A1  12/2009 Schweighoffer et al.

FOREIGN PATENT DOCUMENTS

| WO | 9921890 A1 | 5/1999 |
| WO | 03072041 A2 | 9/2003 |
| WO | 2009152463 A2 | 12/2009 |

OTHER PUBLICATIONS

Tiao et al, J Biological Chemistry, 283(45):31005-31011, Nov. 7, 2008.*
PCT International Search Report and Written Opinion, Application No. PCT/EP2017/067859, dated Jul. 14, 2017, 11 pages.
Steiger Janine L et al., cAMP response element-binding protein, activating transcription factor-4, and upstream stimulatory factor differentially control hippocampal GABABR1a and GABABR1b subunit gene expression through alternative promoters. A Journal of Neurosci, The Society, Washington, DC, US, vol. 24, No. 27, Jul. 7, 2004 (Jul. 7, 2004), pp. 6115-6126, XP009142508, ISSN: 1529-2401, DOI: 10.1523/JNEUROSCI.1200-04.2004, whole document esp. pp. 6115,6124.
Lecat-Guillet, Nathalie, et al. "FRET-Based Sensors Unravel Activation and Allosteric Modulation of the GABAB Receptor." Cell Chemical Biology, vol. 24, No. 3, 2017, pp. 360-370.
Monnier, Carine, et al. "Trans-Activation between 7TM Domains: Implication in Heterodimeric GABA B Receptor Activation." EMBO Journal, vol. 30, No. 1, 2011, pp. 32-42.
New D.C, et al. "GABAB Heterodimeric Receptors Promote Ca2 Influx via Store-Operated Channels in Rat Cortical Neurons and Transfected Chinese Hamster Ovary Cells." Neuroscience, vol. 137, No. 4, 2006, pp. 1347-1358.
Podobnik, Marjetka, et al. "How to Study Protein-Protein Interactions." Acta Chimica Slovenica, vol. 63, No. 3, 2016, pp. 424-439.
Syafrizayanti, C.B, et al. "Methods for Analyzing and Quantifying Protein-Protein Interaction." Expert Review of Proteomics. 11.1 (2014): 107-120.

* cited by examiner

*Primary Examiner* — Kimberly Ballard
*Assistant Examiner* — Stacey N MacFarlane
(74) *Attorney, Agent, or Firm* — Patent Law Works, LLP

(57) ABSTRACT

The present invention relates to the field of disorders of the central nervous system, in particular neurological and psychiatric disorders, and the prevention and/or treatment thereof. In particular, the present invention relates to the finding that soluble amyloid precursor protein a (sAPPα) presents a particular binding site, which allows for binding to the $GABA_BR1a$ receptor, thereby causing an agonistic effect through specific binding to Sushi domain 1 of $GABA_BR1a$. As a result, the frequencies of excitatory and inhibitory postsynaptic currents are reduced. Accordingly, the invention provides compounds able to interfere with the association of sAPPα with Sushi domain 1 of $GABA_BR1a$ and as such with selective impairment of $GABA_BR1sa$ beneficial in neurological and psychiatric disorders. The invention as well provides methods and (high content) screening assays for the production of said compounds.

6 Claims, 17 Drawing Sheets
(17 of 17 Drawing Sheet(s) Filed in Color)
Specification includes a Sequence Listing.

A

B

A

B

C

A

B

ExD = extension domain = ED

| BAD AVG GOOD |

```
APPmouse    MLPS------------LALLLLAAWTVRALEVP-----TDGNAG---LLAEPQIANPCGRLNENNY
APLP1mouse  MGPTSPAARGQGRRWRPPLPLLLPLSLLLLRAQLAVGN-LAVGSPSAAEAPGSAQVAGLCGRLTLHRDL
APLP2mouse  MAATGTAAAAATGK----LLVLLLIGLTAPAAALAGYIEALAANAGTGFAVAEPQIANFCGRLNMHVNI
cons             *  :**   .              : ::         : *:*:** :*.::

APPmouse    QNGKWESDPSGTKTCIGTKEGILQYCQEVYPELQITNVVEANQPVTIQNWCKR--GRKQCKTHTHIVIP
APLP1mouse  RTGRWEPDPQRSRRCLLDPQRVLEYCRQVYPELHIARVEQAAQAIPMERWCGGTRSGRCAHP-HHEVVP
APLP2mouse  QTGKWEPDPTGTRSCLGTKEEVLQYCQEIYPELQITNVVEANQPVNIDSWCRR--DKRQCKS--HIVIP
cons         .** **     *   :    .**  **:.**** :* * *:***** *  **         * **

APPmouse    YRCLVGEFVSDALLVPDKCRFLHQERMDVCETHLHWHTVAKETCSEKSTNLHDYGMLLPCGIDRFRGVE
APLP1mouse  FHCLPGEFVSEALLVPEGCRFLHQERMDQCESSTRPHQEAQEACSSQGLILHGGGMLLPCGSDRFRGVE
APLP2mouse  FKCLVGEFVSIPVLLVPDNCQFTHQERMEVCEKHQRWHTLVKEACLTEGLTLYSYGMLLPCGVDQFHETE
cons         :** ***** .  *:**:.*:* ****: **.   :*:   :*:   ::  .********* *:*   *
                                    Extension Domain
APPmouse    FVCCPLAEESDSVDSADAEEIDSDVWWGGADTDYADGSEDKVVEVAEEEEVADVEEEEADD-DEDVEDG
APLP1mouse  YVCCPPPATPNPSGMAAGDPSTRSWPLGGRAEGGEDEEE----V--------------------EST
APLP2mouse  YVCCPQTKTVDSDSTMSKEEEEEERDEEDEEEDYDLDKS----EFPTEADLEDFTEAAADEEEEDEEEG
cons        :****                                                                *

APPmouse    DEVEEEA------EEPYEEATERTTSTATTTTTTTESVEEVVREPTTAASTPDAVDKYLETPGDENEHA
APLP1mouse  PQPVDDYFVEPPQAEEEEEEEEERAPPPSSHTP-----VMVSRVTPTPRPTD-GVDVYFEMPGEIGEHE
APLP2mouse  EEVVEDRDYYIDPFKGDDYNEENPTEPSSEGTISDKEIVHDVRVPPTPLPTN-DVDVYFETSADDNEHA
cons         ..: .          ::.   :.    *          : :*:. *.*  *  **. :  .   **

APPmouse    HFQKAKERLEAKHRERMSQVMREWEEAERQAKNLPKADKKAVIQHFQERVESLEQEAANEPQQLVETHM
APLP1mouse  GFLRAKMDLEEPRRGINEVMREWAMADSQSKNLPKADRQALNEHFQSILQTLEDQVSGERQRLVETHA
APLP2mouse  RFQKAKEQLEIRHRNRMERVKKEWEEAERQAKNLPKTEPQTLIDHTDAMVKALEREAASEKQQLVETHL
cons         * **    :  ..*: :  :.:**  ** :****::   : :*   ::.*** ::. :***:**

APPmouse    ARVEAMLNDRRRLALENYITALQAVPPRPHHVTNMLKKYVRAEQKDRQHTLKHFEHVRMVDPKKAAQIR
APLP1mouse  TRVIALMDQRRAALEGFLAALQGDPPQAERVLRALRRYLRAEQKEQRHTLRHYQHAAVDPEKACQMR
APLP2mouse  ARVEAMLNDRRRIALENYLAALQSDPPRPHRILQALRRYVRAENKDRLHTIRHYQHVLAVDPEKAAQMR
cons        :** *::*:** ** :* : ***. .** *.:: :*::*: ***:::::::*:  ::*:**:** :*

APPmouse    SQVMTHLRVIYERMNQSLSLLYNVPAVAEEIQDEVDELLQKEQNYSDDVLANMISEPR-ISYGNDALMP
APLP1mouse  PVQTHLRVIEERMNQSLGLLDQMPHLAQELRPQIQELLL-AEHLGPSELDASVPGSSSEDKGS-----
APLP2mouse  SQVMTHLRVIEERMNQSLSLLYKVPSVAQEIQEEIDELLQ-EQRADMDQFTSSISEKP-VDVR------
cons            ***:** ** ****.**    *  *:*  : :***:   :  .  ::  . .

APPmouse    SLTETKTTVELLPVNGEFSLDDLQPWHPFGVDSVPANTENEVEPVDARPAADRGLTTRPGSGLTNIKTE
APLP1mouse  --LQPPESKDDPPVT----------LFKGSTDQESSSGIREKLTPLEDYEQKVNASAPRG---------
APLP2mouse  --VSSEESEEIPPFH----P-----LHPFPGLSENEGSGMAEDGGLIGAEERVINSNKNDERMVIDE
cons           .  *.   .         *    .:  .                                .
                                                                    TM domain
APPmouse    EISEVKMDAEFGHDSGFEVRHQKLVFFAEDVGSNKGAIIGLMVGGVVIATVIVITLVMLKKK-QYTSIH
APLP1mouse  -----SPFHSSDIQRDELAP-------SGTGVSREALSGLLIMGAGGGSLIVLSLLLLRKKKPYGTIS
APLP2mouse  TLDVKEMIFNAERVQGLEEEPESVGPLREDFSLSSNALIGLLVIAVAIATVIVISLVMLRKR-QYGTIS
cons              :  .   .  : .                .*: *:::. . .: ::*.:*:*:*:. ** **
```

```
                           Extension Domain (ExD)
                        ─────────────────────────────────────
APP_human    EESDNVDSADAEEDDSDVWWGGADTDYADGSEDKVV
APLP1_human  GTPDPSGTAVGD-PSTRSWPPGSRV-----------
APLP2_human  KIIGSVSKEEEEEDEEEEEEDEEEDYDVYK----S
                           204                220

APP_human    EESDNVDADAEDD  V       DTD ADGSEDKVV
APP_pig      EESDNIDADAEDD  V       DTD ADGSEDKVV
APP_chick    EESDNLDADADDD  V       DAD ADGSDDKVV
APP_rat      EESDSIDADAEDD  V       DTD ADGGEDKVV
APP_mouse    EESDSVDADAEDD  V       DTD ADGGEDKVV
APP_frog     EESESFDADA-DD  A       DAD VDRSDDKAV
APPa_fish    AG-KESEAAVEDD  V       EAD TENSMTRDA
APPb_fish    EQ-KDLDEEQEAN  V       ETE TDASVLKEQ
```

THERAPEUTIC AGENTS FOR NEUROLOGICAL AND PSYCHIATRIC DISORDERS

FIELD OF THE INVENTION

The present invention relates to the field of disorders of the central and peripheral nervous system, in particular neurological and psychiatric disorders, and the prevention and/or treatment thereof. In particular, the present invention relates to the finding that soluble amyloid precursor protein a (sAPPα) presents a particular binding site, which allows for binding to the $GABA_BR1a$ receptor, thereby causing an agonistic effect through specific binding to sushi domain 1 of $GABA_BR1a$. As a result, the frequencies of excitatory and inhibitory postsynaptic currents are reduced. Accordingly, the invention provides compounds able to interfere with the association of sAPPα with Sushi domain 1 of $GABA_BR1a$ and as such with selective impairment of $GABA_BR1a$ beneficial in neurological and psychiatric disorders. The invention as well provides methods and (high content) screening assays for the production of said compounds.

BACKGROUND OF THE INVENTION $GABA_B$ receptors are the G-protein coupled receptors for γ-aminobutyric acid (GABA), the main inhibitory neurotransmitter in the CNS. $GABA_B$ receptors mediate pre- and postsynaptic inhibition in the nervous system and are implicated in a variety of neurological and psychiatric disorders, including cognitive impairments, anxiety, depression, schizophrenia, epilepsy, obsessive compulsive disorder, addiction and pain (Calver et al., Neurosignals 11, 2002; Bettler et al., Physiol Rev 84, 2004).

Presynaptic $GABA_B$ receptors inhibit the release of GABA (autoreceptors) and other neurotransmitters (heteroreceptors), while postsynaptic $GABA_B$ receptors inhibit neuronal excitability by activating K+ channels. Receptor subtypes are based on the subunit isoforms $GABA_B1a$ and $GABA_B1b$, both of which combine with $GABA_B2$ subunits to form two heteromeric receptors, $GABA_B(1a, 2)$ and $GABA_B(1b, 2)$ (Marshall et al., Trends Pharmacol Sci 20, 1999). Most if not all neurons in the CNS coexpress $GABA_B(1a, 2)$ and $GABA_B(1b, 2)$ receptors. The $GABA_B1a$ and $GABA_B1b$ subunit isoforms derive from the same gene by alternative promoter usage and solely differ in their N-terminal ectodomains (Kaupmann et al., Nature 386, 1997; Steiger et al., J Neurosci 24, 2004). $GABA_B1a$ contains at its N terminus two sushi domains (SDs) that are lacking in $GABA_B1b$ (Hawrot et al., FEBS Lett 432, 1998). SDs, also known as complement control protein modules or short consensus repeats, are conserved protein interaction motifs present in proteins of the complement system, in adhesion molecules and in G-protein-coupled receptors (Lehtinen et al., J Mol Biol 344, 2004; Perrin et al., Acad Sci 1070, 2006).

Pharmacological tools that distinguish $GABA_B(1a, 2)$ and $GABA_B(1b, 2)$ receptors are lacking; however, the native roles of $GABA_B1a$ and $GABA_B1b$ were dissociated using $GABA_B1a-/-(1a-/-)$ and $GABA_B1b-/-(1b-/-)$ mice, which express one or the other isoform (Vigot, R. et al, Neuron 50, 2006). These mice revealed that heteroreceptors incorporate the $GABA_B1a$ subunit, whereas autoreceptors and postsynaptic $GABA_B$ receptors incorporate $GABA_B1a$ or $GABA_B1b$ subunits (Vigot, R. et al, Neuron 50, 2006; Shaban, H. et al., Nat. Neurosci. 9, 2006; Ulrich, D., and Bettler, B., Curr. Opin. Neurobiol. 17, 2007). This suggests that the SDs of $GABA_B1a$ bind to protein(s) that localize heteroreceptors at glutamatergic terminals.

The non-selective impairment of $GABA_B1a$ and $GABA_B1b$ receptors by baclofen as the prototypical $GABA_BR$ agonist in clinical use has been described by Jacobson et al. (Jacobson et al., J Neurosci., 2006). This study suggests that $GABA_B1a$ and $GABA_B1b$ isoforms are functionally relevant molecular variants of the $GABA_B$ receptor subunit, which are differentially involved in specific neurophysiological processes and behaviors. The $GABA_B$ receptor agonists baclofen and γ-hydroxybutyrate are unable to pharmacologically discriminate between the two isoforms though. Despite the reported involvement of $GABA_B$ receptors in mental health disorders, the clinical use of $GABA_BR$ agonists is currently limited to the treatment of narcolepsy, neuropathic pain, spasticity and dystonia (Gassmann, M. and Bettler, B., Nature Reviews Neuroscience 13, 2012). One reason for this is that the main therapeutic effect of baclofen is muscle relaxation, which is an unwanted, adverse effect for psychiatric indications. As the sequence of the $GABA_B1a$ and $GABA_B1b$ isoforms differ primarily in the N terminus, and not in the region coding for the ligand binding domain, there is a need for future studies focusing on strategies to uncover novel interaction sites at either receptor isoform to enable specific pharmaceutical intervention.

We recently unraveled how to specifically modulate the $GABA_B1a$ receptor. Surprisingly, we found that the soluble amyloid precursor protein a (sAPPα) is able to activate this receptor. Our findings showed that sAPPα specifically interacts with the sushi domain 1 of $GABA_BR1a$ via its extension domain. We successfully minimized the number of amino acids being crucial for interaction and based on this epitope, specific agonists, antagonists and modulators of the $GABA_B1a$ receptor can be provided for the first time. Our approach displays a major step forward in the development of specific modulators of the $GABA_B1a$ receptor and can directly be utilized for the development of novel therapeutics for the treatment of neurological and psychiatric disorders.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following drawings are illustrative of one or more embodiments of the invention and not illustrative of the invention.

DETAILED DESCRIPTION

Figure 1:
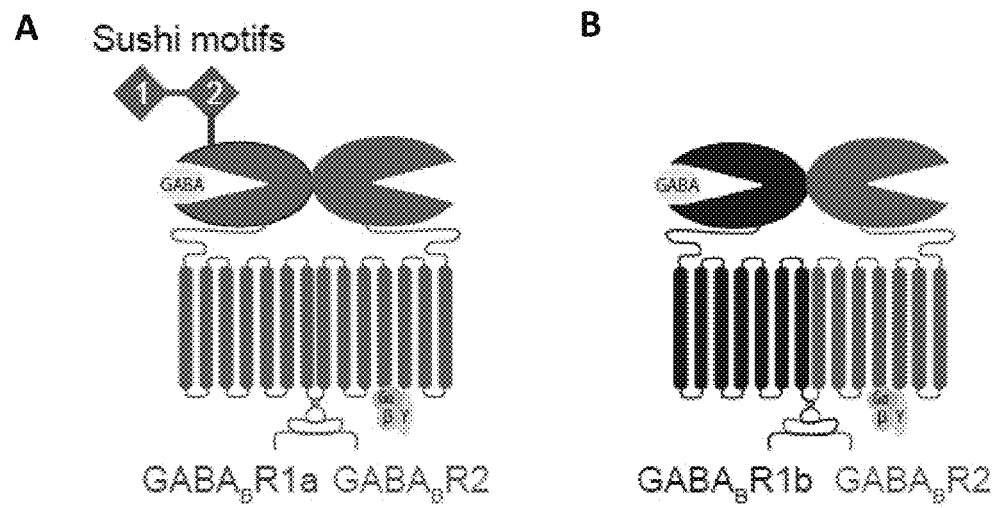
FIG. 1: APPα interacts with $GABA_BR1a$. A-B. Schematic representation of $GABA_BR$ subunits and isoforms. $GABA_BR1a$ (A) differs from $GABA_BR1b$ (B) by the presence of the sushi motifs. C-D. Confocal images (C) and quantification of the interaction between Fc-sAPPα and $GABA_BR$ isoforms. Purified Fc-sAPPα were exogenously applied to $GABA_BR$-transfected HEK293 cells and bound Fc-sAPPα was determined by immunofluorescence. Fc-sAPPα only interacts with $GABA_BR1a$ and the sushi domains in $GABA_BR1a$ mediate its binding to the APP ectodomain. E. Immunoblot of rat brain fractionations probed for APPα family members and pre-(Syp) or post-(PSD-95 and NR2A) synaptic markers. F. Super-resolution images of mouse hippocampal sections immunostained for APPα with presynaptic (VGLUT1—excitatory; VGAT—inhibitory) and postsynaptic (PSD-95—excitatory; Gephyrin—inhibitory) markers.
Figure 1:
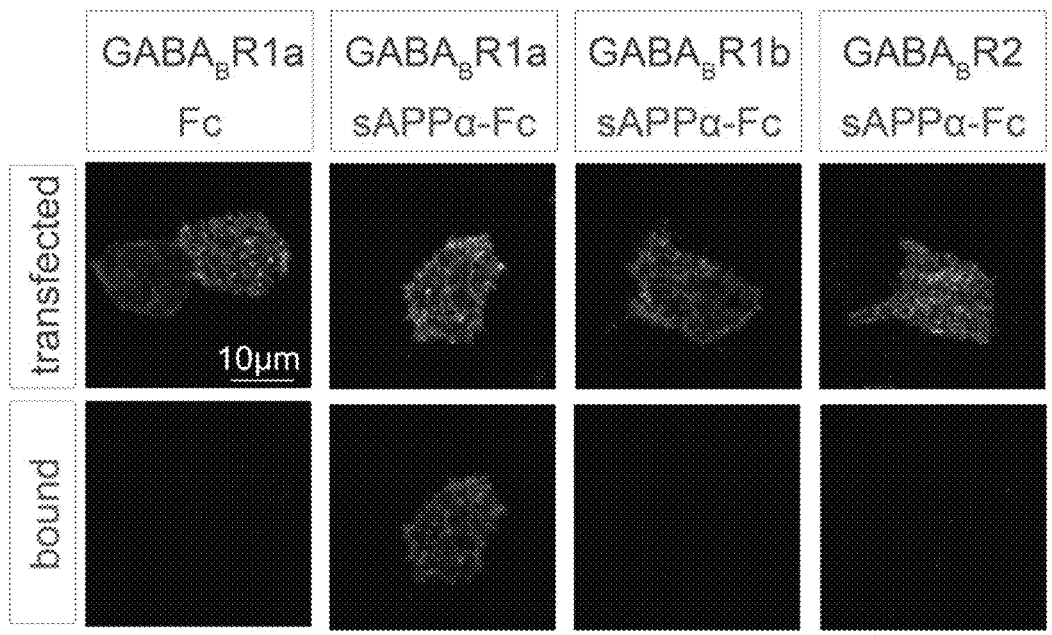
Figure 1:
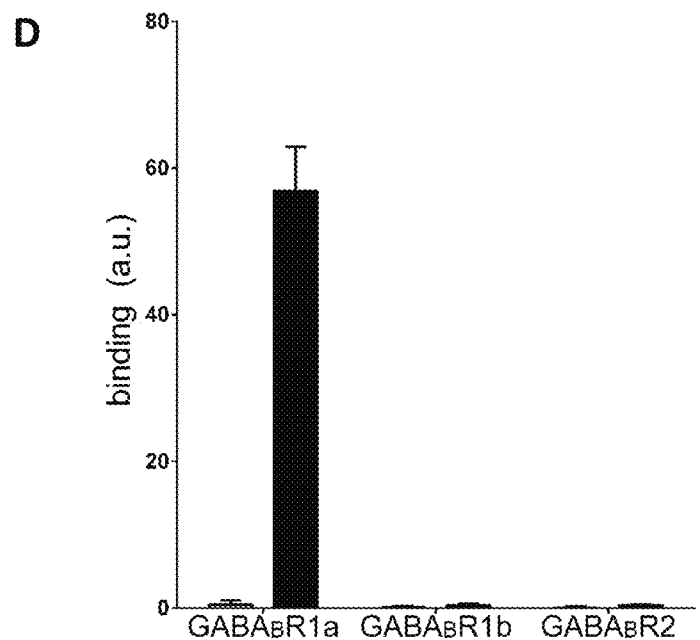
Figure 1:
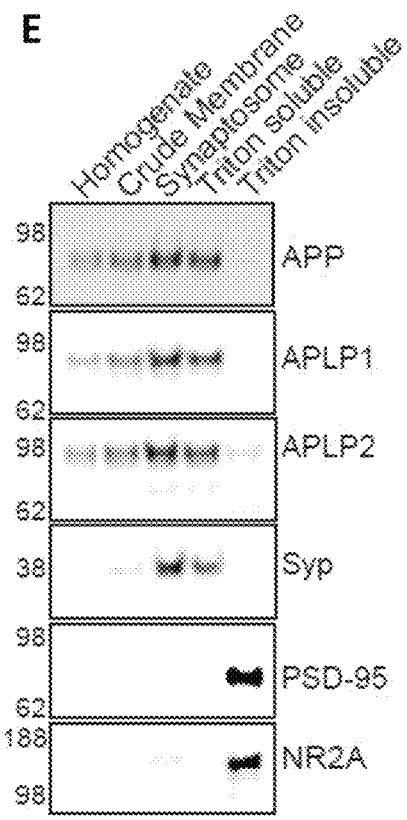
Figure 1:
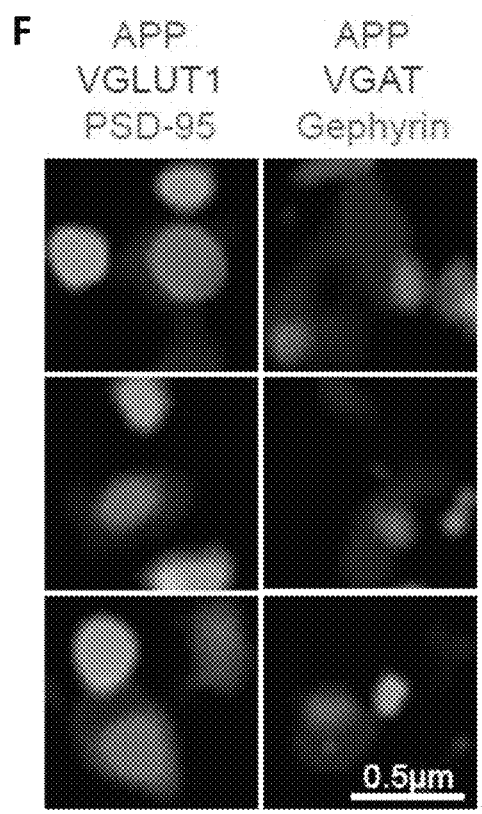

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4$^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"Homologue", "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

The term "amino acid identity" as used herein refers to the extent that sequences are identical on an amino acid-by-amino acid basis over a window of comparison. Thus, a "percentage of sequence identity" is calculated by comparing two optimally aligned sequences over the window of comparison, determining the number of positions at which the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

By "isolated" is meant material that is substantially or essentially free from components that normally accompany it in its native state. For example, a "peptide sequence", as used herein, refers to a peptide, which has been purified from the molecules which flank it in a naturally-occurring state, e.g., an extension domain of APP which has been removed from the molecules present in the production host that are adjacent to said peptide. An isolated extension domain of APP can be generated by amino acid chemical synthesis or can be generated by recombinant production. Another example concerns an isolated neuronal cell, which refers to a neuronal cell which has been extracted and purified from the naturally-occurring state, involving tissue. An isolated neuronal cell preparation can be obtained from several neuronal tissue types using for example specialized commercial kits that make use of proteases to digest intercellular protein junctions followed by gentle mechanical disruption to liberate individual cells, or for instance but not limited to the exemplified method.

The term "treatment" or "treating" or "treat" can be used interchangeably and are defined by a therapeutic intervention that slows, interrupts, arrests, controls, stops, reduces, or reverts the progression or severity of a sign, symptom, disorder, condition, or disease, but does not necessarily involve a total elimination of all disease-related signs, symptoms, conditions, or disorders. However, it will be understood that the aforementioned terms do not imply that symptoms are present.

The terms "subject" as used herein, refers to any subject, particularly a vertebrate subject, and even more particularly a mammalian subject, for whom therapy or prophylaxis is desired. A "subject" as used herein refers to an animal that can develop neurological and psychiatric disorders. Typically, the animal is a mammal. Most particularly, the subject is a human.

The term "antibody" as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Worn and Pluckthun, 2001; Koerber et al., 2015.).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "single-domain antibody", herein referred to as "nanobody", is an antibody fragment consisting of a single monomeric variable antibody domain. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

As used herein, the term "method" comprises a "high content screening (HCS)" of suitable test compounds. In some instances, HCS is a screening method that uses an in vitro system to perform a series of experiments as the basis for high throughput compound discovery. Typically, HCS is an automated system to enhance the throughput of the screening process. However, the present invention is not limited to the speed or automation of the screening process. In another embodiment of the invention, the HCS assay provides for a high throughput assay. Preferably, the assay provides automated screening of thousands of test compounds.

"Compound" means any chemical or biological compound, including simple or complex organic and inorganic molecules, peptides, peptido-mimetics, proteins, antibodies, carbohydrates, nucleic acids or derivatives thereof. The term "compound" or "test compound" is used herein in the context of a "drug candidate compound" or a "candidate compound for Lead optimization" in therapeutics, described in connection with the methods of the present invention. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates.

It is an object of the invention to provide therapeutic agents, particularly pharmaceutical compositions, comprising compounds specifically impairing the $GABA_B1a$ receptor. Additional compounds can be identified by monitoring the activity of a functional $GABA_B1a$ receptor expressed in a cell when a test compound is administered to said cell. Therefore, according to a first aspect, the application provides a peptide as depicted in SEQ ID NO: 1 or a homologue thereof of at least 95% amino acid identity. SEQ ID NO: 1 depicts the amino acid sequence of the extension domain of human sAPPα.

```
SEQ ID NO: 1: Extension domain of human sAPPα (33
amino acids):
NVDSADAEEDDSDVWWGGADTDYADGSEDKVVE
```

According to one embodiment, the peptide sequence depicted in SEQ ID NO: 1 or a homologue thereof of at least 95% amino acid identity refers to an isolated peptide. According to another embodiment, a peptide sequence depicted in SEQ ID NO: 1 or a homologue thereof of at least 95% amino acid identity refers to an isolated peptide obtained by purification from APP. In another embodiment a peptide sequence depicted in SEQ ID NO: 1 or a homologue thereof of at least 95% amino acid identity is generated by chemical amino acid synthesis. According to another embodiment SEQ ID NO: 1 or a homologue thereof of at least 95% amino acid identity is generated by recombinant production.

In a second aspect, the application provides a peptide fragment derived from a peptide as depicted in SEQ ID NO: 1 or a homologue thereof of at least 95% amino acid identity, said peptide fragment consist of a sequence as depicted in SEQ ID NO: 2 or a homologue thereof of at least 95% amino acid identity or as depicted in SEQ ID NO: 3 or a homologue thereof of at least 95% amino acid identity. SEQ ID NO: 2 depicts a 17 amino acid long sequence fragment (D204-G220) of the extension domain of human sAPPα, while SEQ ID NO: 3 depicts a 9 amino acid long sequence fragment (D204-G212) of the extension domain of human sAPPα.

```
SEQ ID NO: 2: Fragment (D204-G220) of the
extension domain of human sAPPα:
DDSDVWWGGADTDYADG SEQ ID NO: 3: Fragment (D204-G212) of the
extension domain of human sAPPα:
DDSDVWWGG SEQ ID NO: 4: Fragment (G210-G220) of the
extension domain of human sAPPα:
GGADTDYADG
```

In a third aspect, the application provides a peptidomimetic generated from the peptide as depicted 15 in SEQ ID NO: 1 or a homologue thereof of at least 95% amino acid identity. In one embodiment the application provides a peptidomimetic generated from a peptide fragment derived from the peptide as depicted in SEQ ID NO: 1 or a homologue thereof of at least 95% amino acid identity, said peptide fragment consists of a sequence as depicted in SEQ ID NO: 2 or a homologue thereof of at least 95% amino acid identity or as depicted in SEQ ID NO: 3 or a homologue thereof of at 20 least 95% amino acid identity.

According to the present application, the degree of identity, between a given reference amino acid sequence and an amino acid sequence which is a homologue of said given amino acid sequence will preferably be at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The degree of identity is 25 given preferably for an amino acid region which is at least 10%, at least 20%, at least 30%, at least 40%, at least 50%, at least 60%, at least 70%, at least 80%, at least 90% or 100% of the entire length of the reference amino acid sequence. For example, if the reference amino acid sequence consists of 200 amino acids, the degree of identity is given preferably for at least 20, at least 40, at least 60, at least 80, at least 100, at least 120, at least 140, at least 160, at least 180, or 200 amino acids, preferably continuous amino acids. In the embodiments, the degree/percentage of similarity or identity is given for the entire length of the reference amino acid sequence.

Thus in a particular embodiment, a peptide sequence depicted in SEQ ID NO: 1 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity is provided. In further particular embodiments, the application provides a peptide fragment derived from the peptide sequence depicted in SEQ ID NO: 1 or a homologue thereof of at least 95% amino acid identity, said peptide sequence fragment is depicted in SEQ ID NO: 2 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity or as depicted in SEQ ID NO: 3 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity. In particular embodiments, a peptidomimetic generated from a peptide sequence as depicted in SEQ ID NO: 1 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity is provided. In yet another particular embodiment, a peptidomimetic generated from a peptide fragment derived from a peptide sequence as depicted in SEQ ID NO: 1 or a homologue thereof of at least 95% amino acid identity in provided, wherein said peptide sequence fragment is depicted in SEQ ID NO: 2 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity or as depicted in SEQ ID NO: 3 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity.

Peptidomimetics or non-natural peptides provide an alternative source of potent and selective Protein-Protein Interaction (PPI) modulators and occupy the chemical gap between small molecules and biologics, such as antibodies. Moreover, peptidomimetics suitably cover the chemical space required to modulate PPIs. Envisaged herein are peptidomimetics which mimic in the structure to peptide and the biological activity while bioavailability, bio-stability, bioefficiency as well as the half-life of the activity can be increased compared to the peptide they refer to. Preferably, peptidomimetics according to the invention provide enhanced bioavailability, bio-stability, bioefficiency and half-life activity when compared to the peptide they refer to. Peptidomimetics in the scope of the present invention allow for greater distribution within the target tissues such as the brain for improved therapeutic efficacy, higher stability at ambient temperature leading to better storage properties, lower cost of goods and easier regulatory clearance due to lack of issues related to purity such as contamination by cellular materials. Preferably, peptidomimetics of the present invention show high permeability across the blood-brain barrier. Peptidomimetics according to the invention offer advantages, such as high stability and low toxicity and immunogenicity, when compared to currently used therapeutic approaches.

In a fourth aspect, a molecule is provided wherein said molecule comprises the peptide as depicted in SEQ ID NO: 1 or a homologue thereof of at least 95% amino acid identity or comprises a peptidomimetic generated from said peptide as depicted in SEQ ID NO: 1 or a homologue thereof of at least 95% amino acid identity, said molecule further comprises a half-life extension entity and/or an entity that facilitates said molecule to cross the blood brain barrier. In one embodiment, a molecule is provided wherein said molecule comprises a peptide fragment derived from SEQ ID NO: 1 or a homologue thereof of at least 95% amino acid identity or comprises a peptidomimetic generated from a peptide fragment derived from SEQ ID NO: 1 or a homologue thereof of at least 95% amino acid identity, wherein said peptide fragment is depicted in SEQ ID NO:2 or a homologue thereof of at least 95% amino acid identity or depicted in SEQ ID NO:3 or a homologue thereof of at least 95% amino acid identity and wherein said molecule further comprises a half-life extension entity and/or an entity that facilitates said molecule to cross the blood brain barrier. In particular embodiments, said molecule is a chimeric molecule, a chimeric protein, a dimeric protein, a fusion protein, a composition, a combination, a peptide or a polypeptide.

In a more particular embodiment, the application provides a peptide as depicted in SEQ ID NO: 1 or a homologue from a peptide sequence depicted in SEQ ID NO: 1 or a homologue thereof of at least 95% amino acid identity comprising a molecule which increases the half-life extension. In an alternative embodiment, the application provides a peptidomimetic generated from a peptide sequence depicted in SEQ ID NO: 1 or a homologue thereof of at least 95% amino acid identity comprising a molecule which increases the half-life extension. In another particular embodiment the application provides a peptide fragment derived from a peptide sequence depicted in SEQ ID NO: 1 or a homologue thereof of at least 95% amino acid identity, wherein said peptide fragment is depicted in SEQ ID NO: 2 or a homologue thereof of at least 95% amino acid identity or depicted in SEQ ID NO:3 or a homologue thereof of at least 95% amino acid identity, said peptide fragment further comprising a molecule which increases the half-life extension. In a particular embodiment the invention provides a peptidomimetic generated from a peptide fragment derived from a peptide as depicted in SEQ ID NO: 1 or a homologue thereof of at least 95% amino acid identity, wherein said peptide fragment is depicted in SEQ ID NO: 2 or a homologue thereof of at least 95% amino acid identity or depicted in SEQ ID NO:3 or a homologue thereof of at least 95% amino acid identity, said peptidomimetic further comprising a molecule which increases the half-life extension.

Peptide sequences and peptidomimetics of the invention can be provided as such or can be prepared as a chimeric molecule, dimeric molecule or as a fusion protein. For example, they can be linked to the whole or partial Fc to express in the appropriate peptide sequences, peptidomimetics and antibodies of this invention. Peptide sequences, peptidomimetics and antibodies of this invention can be expressed in the N-terminal or C-terminal of the Fc gene.

Covalently modified peptide sequences, peptidomimetics and antibodies are also included in this invention. Chemically covalent modification includes modifying N- or C-terminal or adding a chemical molecule to other amino acids. Peptides, peptidomimetics and antibodies of the invention can be fused or conjugated to any half-life extension molecule. The term "a half-life extension entity" as used above is equivalent to said half-life extension molecule. Such half-life extension molecules are known by a person skilled in the art and include, for example, not only an Fc region/domain of an immunoglobulin but also albumin, an albumin-binding domain, an immunoglobulin-binding domain, an FcRn-binding motif, and a polymer. Particularly preferred polymers include polyethylene glycol (PEG), hydroxyethyl starch (HES), hyaluronic acid, polysialic acid and PEG-mimetic peptide sequences. For modification of peptides, peptidomimetics and antibodies of the invention activated PEG with molecular weight of 5,000-100,000 can be used for the purpose of prolonging their half-life time. Detailed protocols can be seen in Greenwald et al., Bioorg. Med.Chem. Lett. 1994, 4, 2465; Caliceti et al., IL Farmaco, 1993, 48,919; Zalipsky and Lee, Polyethylene Glycol Chemistry: Biotechnical and Biomedical Applications, J. M. Harris, Plenus Press, New York (1992). Multi-arm branched PEG is preferred. Also within the scope of this application are modifications preventing aggregation of the peptides, peptidomimetics and antibodies. These modifications are also known to the skilled person and include, for example, the substitution of one or more hydrophobic amino acids, preferably surface-exposed hydrophobic amino acids, with one or more hydrophilic amino acids. In one embodiment, the peptides, peptidomimetics and antibodies according to the invention or the immunogenic variant thereof or the immunogenic fragment of any of the foregoing, comprises the substitution of up to 10, 9, 8, 7, 6, 5, 4, 3 or 2, preferably 5, 4, 3 or 2, hydrophobic amino acids, preferably surface-exposed hydrophobic amino acids, with hydrophilic amino acids. Preferably, other properties of the peptides, peptidomimetics and antibodies according to the invention, e.g., their immunogenicity, are not compromised by such substitution. Still other techniques of formulation as nanotechnology and aerosol and inhalant are also within the scope of this invention.

In a particular embodiment the invention provides a peptide as depicted in SEQ ID NO: 1 or a homologue thereof of at least 95% amino acid identity, said peptide further comprising a molecule which enables the peptide to cross the blood brain barrier.

A molecule also referred to as an element herein, which enables the peptides, peptidomimetics and antibodies of the invention to cross the blood brain barrier can be a cell penetrant carrier, wherein said cell penetrant carrier can enter a cell through a sequence which mediates cell penetration (or cell translocation). In the latter case said peptides, peptidomimetics and antibodies of the invention are modified through the recombinant or synthetic attachment of a cell penetration sequence. Thus, the molecule (e.g. as a peptide) may be further fused or chemically coupled to a sequence facilitating transduction of the fusion or chemical coupled proteins into prokaryotic or eukaryotic cells. Sequences facilitating protein transduction are known to the person skilled in the art and include, but are not limited to Protein Transduction Domains. It has been shown that a series of small protein domains, termed protein transduction domains (PTDs), cross biological membranes efficiently and independently of transporters or specific receptors, and promote the delivery of peptides and proteins into cells. Preferably, said sequence is selected from the group comprising TAT protein from human immunodeficiency virus (HIV-1), a polyarginine sequence, penetratin and a short amphipathic peptide carrier, Pep-1. Still other commonly used cell-permeable peptides (both natural and artificial peptides) are disclosed in Joliot A. and Prochiantz A. (2004) Nature Cell Biol. 6 (3) 189-193. The list of molecules enabling the peptides, peptidomimetis and antibodies of this invention to cross the blood brain barrier is not limited by the above given examples and references. Any molecule or element which enables the peptides, peptidomimetics and antibodies of the invention to cross the blood brain barrier is in the scope of the present invention. Such a molecule or element is referred to as "entity that facilitates a molecule to cross the blood brain barrier", as used above.

In a particular embodiment the invention provides a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity, or depicted in SEQ ID NO: 3 or a homologue thereof of at least 95% amino acid identity, further comprising a molecule which enables the peptide to cross the blood brain barrier. In a more particular embodiment, said peptide fragment further comprises a molecule which increases the half-life extension of said peptide sequence.

In another particular embodiment the invention provides a peptidomimetic generated from a peptide as depicted in SEQ ID NO: 1 or a homologue thereof of at least 95% amino acid identity, said peptidomimetic further comprising a molecule which enables the peptidomimetic to cross the blood brain barrier. In a more particular embodiment, said peptidomimetic further comprises a molecule which increases the half-life extension of said peptidomimetic.

In another particular embodiment the invention provides a peptidomimetic generated from a peptide fragment derived from a peptide as depicted in SEQ ID NO: 1 or a homologue thereof of at least 95% amino acid identity, said peptide sequence fragment is depicted in SEQ ID NO: 2 or a homologue thereof of at least 95% amino acid identity or depicted in SEQ ID NO: 3 or a homologue thereof of at least 95% amino acid identity, said peptidomimetic further comprising a molecule which enables the peptidomimetic to cross the blood brain barrier. In a more particular embodiment, said peptidomimetic further comprises a molecule which increases the half-life extension of peptidomimetic.

In a fifth aspect, the application provides a peptide as depicted in SEQ ID NO: 1 or a homologue thereof of at least 95% amino acid identity further comprising at least one D-alanine at the N-terminus and/or the C-terminus. In a more particular embodiment, said peptide sequence further comprises a molecule which increases the half-life extension of said peptide sequence and/or a molecule which enables the peptide sequence to cross the blood brain barrier.

In a particular embodiment the invention provides a peptide fragment derived from a peptide sequence depicted in SEQ ID NO: 1 or a homologue thereof of at least 95% amino acid identity, said peptide fragment is depicted in SEQ ID NO: 2 or a homologue thereof of at least 95% amino acid identity or depicted in SEQ ID NO: 3 or a homologue thereof of at least 95% amino acid identity further comprising at least one D-alanine at the N-terminus and/or the C-terminus. In a more particular embodiment, said peptide fragment further comprises a molecule which increases the half-life extension of said peptide and/or a molecule which enables the peptide fragment to cross the blood brain barrier.

In another particular embodiment the invention provides a peptidomimetic generated from a peptide as depicted in SEQ ID NO: 1 or a homologue thereof of at least 95% amino acid identity further comprising at least one D-alanine at the N-terminus and/or the C-terminus. In a more particular embodiment, said peptidomimetic further comprises a molecule which increases the half-life extension of said peptidomimetic and/or a molecule which enables the peptidomimetic to cross the blood brain barrier.

In another particular embodiment the invention provides a peptidomimetic generated from a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity, or depicted in SEQ ID NO: 3 or a homologue thereof of at least 95% amino acid identity further comprising at least one D-alanine at the N-terminus and/or the C-terminus. In a more particular embodiment, said peptidomimetic further comprises a molecule which increases the half-life extension of said peptidomimetic and/or a molecule which enables the peptidomimetic to cross the blood brain barrier.

In a sixth aspect, a nucleic acid molecule is provided, wherein said nucleic acid molecule encodes one of the above described peptides. In particular embodiments, a nucleic acid molecule is provided, wherein said nucleic acid molecule encodes one of the above described peptide fragments.

As used herein, the terms "nucleic acid", "polynucleotide", "polynucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The polynucleotide molecule may be linear or circular. The polynucleotide may comprise a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. A nucleic acid that is up to about 100 nucleotides in length, is often also referred to as an oligonucleotide.

In a seventh aspect, the invention provides a pharmaceutical composition comprising a peptide as depicted in SEQ ID NO: 1 or a homologue thereof of at least 95% amino acid identity and a pharmaceutically acceptable carrier.

Pharmaceutical compositions comprising peptides, peptidomimetics and antibodies of the invention and a pharmaceutically acceptable carrier can be utilized to achieve the desired pharmacological effect by administration to a patient in need thereof. A patient, for the purpose of this invention, is a mammal, particularly a human, in need of treatment for the particular condition or disease. Therefore, the present invention includes pharmaceutical compositions that are comprised of a pharmaceutically acceptable carrier and a pharmaceutically effective amount of peptides, peptidomimetics and antibodies of the invention and a pharmaceutically acceptable carrier. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of peptides, peptidomimetics and antibodies of the invention and a pharmaceutically acceptable carrier is preferably that amount which produces a result or exerts an influence on the particular condition being treated. The peptides, peptidomimetics and antibodies of the invention and a pharmaceutically acceptable carrier can be administered with pharmaceutically acceptable carriers well known in the art using any effective conventional dosage form, including immediate, slow and timed release preparations, orally, parenterally, topically, nasally, ophthalmically, intrathecally, intracerebroventricularly, sublingually, rectally, vaginally, and the like. Still other techniques of formulation as nanotechnology and aerosol and inhalant are also within the scope of this invention.

The peptides, peptidomimetics and antibodies of this invention can be used as a medicament. One skilled in the art can prepare a pharmaceutically effective formulation according to common methods, which contains effective amount of the peptide sequences, peptidomimetics and antibodies as well as pharmaceutically acceptable carriers.

When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN™, PLURONICS™ or PEG and the like.

The preparation containing the peptides, peptidomimetics and antibodies of this invention should be sterilized before injection. This procedure can be done using sterile filtration membranes before or after lyophilization and reconstitution.

The pharmaceutical composition is usually filled in a container with sterile access port, such as an i.v. solution bottle with a cork. The cork can be penetrated by hypodermic needle.

The pharmaceutical compositions of this invention can be administrated through normal ways, including but not limited to intravenous injection or infusion, intra-abdominal injection, intracerebroventricular injection, intramuscular injection, intra-arterial injection or infusion, locally or through sustained release systems.

The dosage and concentration can be adjusted according to actual situation. One skilled in the art should know how to choose proper dosage and injection means according to actual situation. The animal experiments in this invention show credible instructions for the effective amount in human body.

The principle for adjusting between different species such as mice and human can be seen in Mordenti, J. and Chappell, W. "The use of interspecies scaling in toxicokinetics" In Toxicokinetics and New Drug Development, Yacobi et al.; Pergamon Press, New York 1989, pp. 42-96.

The dosage should be adjusted according to different injection means. Direction for certain specific dosage and way of administration can be seen in U.S. Pat. No. 4,657,760, 5,206,344 or 5,225,212.

In a specific embodiment the micro-capsule containing the peptides, peptidomimetics and antibodies of the invention can also be used as a sustained release system. The sustained release system of peptides, peptidomimetics and antibodies of this invention can be prepared with PLGA which has good biologically compatibility and degradability. Lactic acid and glycolic acid, the degrading products of PLGA, can be cleared quickly in human body. Furthermore, the degradability of the polymer can vary from several months to several years according to its molecular weight and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

In a particular embodiment the invention provides a pharmaceutical composition comprising a peptide fragment derived from a peptide as depicted in SEQ ID NO: 1 or a homologue thereof of at least 95% amino acid identity and a pharmaceutically acceptable carrier, said peptide fragment is depicted in SEQ ID NO: 2 or a homologue thereof of at least 95% amino acid identity or as depicted in SEQ ID NO: 3 or a homologue thereof of at least 95% amino acid identity.

In another particular embodiment, the application provides a pharmaceutical composition comprising a peptidomimetic and a pharmaceutically acceptable carrier, said peptidomimetic is generated from the peptide as depicted in SEQ ID NO: 1 or a homologue thereof of at least 95% amino acid identity. In one embodiment the application provides a pharmaceutical composition comprising a peptidomimetic and a pharmaceutically acceptable carrier, said peptidomimetic is generated from a peptide fragment derived from the peptide as depicted in SEQ ID NO: 1 or a homologue thereof of at least 95% amino acid identity, said peptide fragment consists of a sequence as depicted in SEQ ID NO: 2 or a homologue thereof of at least 95% amino acid identity or as depicted in SEQ ID NO: 3 or a homologue thereof of at least 95% amino acid identity.

In particular embodiments, a pharmaceutical composition is provided comprising a pharmaceutical acceptable carrier and a peptide as depicted in SEQ ID NO: 1 or a homologue thereof of at least 95% amino acid identity further comprising at least one D-alanine at the N-terminus and/or the C-terminus and/or further comprising a molecule which increases the half-life extension of said peptide and/or further comprising a molecule which enables the peptide to cross the blood brain barrier.

In other particular embodiments, the invention provides a pharmaceutical composition comprising a pharmaceutical acceptable carrier and a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity or depicted in SEQ ID NO: 3 or a homologue thereof of at least 95% amino acid identity, said peptide fragment further comprising at least one D-alanine at the N-terminus and/or the C-terminus and/or further comprising a molecule which increases the half-life extension of said peptide and/or further comprising a molecule which enables the peptide fragment to cross the blood brain barrier.

In particular embodiments, the invention provides a pharmaceutical composition comprising a pharmaceutical acceptable carrier and a peptidomimetic, said peptidomimetic is generated from a peptide as depicted in SEQ ID NO: 1 or a homologue thereof of at least 95% amino acid identity, said peptidomimetic further comprises at least one D-alanine at the N-terminus and/or the C-terminus and/or further comprises a molecule which increases the half-life extension of said peptidomimetic and/or further comprises a molecule which enables the peptidomimetic to cross the blood brain barrier.

In another particular embodiment the invention provides a pharmaceutical composition comprising a pharmaceutical acceptable carrier and a peptidomimetic, said peptidomimetic generated from a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity, or depicted in SEQ ID NO: 3 or a homologue thereof of at least 95% amino acid identity, said peptidomimetic further comprising at least one D-alanine at the N-terminus and/or the C-terminus and/or further comprising a molecule which increases the half-life extension of said peptidomimetic and/or further comprising a molecule which enables the peptidomimetic to cross the blood brain barrier.

In particular embodiments, a pharmaceutical composition is provided comprising a pharmaceutical acceptable carrier and one of the peptides, or peptide fragments, or peptidomimetics, or antibodies of the application.

In an eight aspect, the application provides a peptide as depicted in SEQ ID NO: 1 or a homologue thereof of at least 95% amino acid identity for use as a medicament. In one embodiment, said peptide for use as a medicament further comprises a molecule that increases the half-life extension. In another embodiment, said peptide for use as a medicament further comprises a molecule that enables said peptide to cross the blood-brain-barrier. In another embodiment, said peptide for use as a medicament further comprises at least one D-alanine at the N-terminus and/or the C-terminus. In another embodiment, said peptide for use as a medicament further comprises a molecule that increases the half-life extension and/or a molecule that enables said peptide to cross the blood-brain-barrier and/or at least one D-alanine at the N-terminus and/or the C-terminus.

In another embodiment, the invention provides a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity, or depicted in SEQ ID NO: 3 or a homologue thereof of at least 95% amino acid identity for use as a medicament. In one particular embodiment, said peptide fragment for use as a medicament further comprises a molecule that increases the half-life extension. In another particular embodiment, said peptide fragment for use as a medicament further comprises a molecule that enables said peptide fragment to cross the blood-brain-barrier. In another particular embodiment, said peptide fragment for use as a medicament further comprises at least one D-alanine at the N-terminus and/or the C-terminus. In another embodiment, said peptide fragment for use as a medicament further comprises a molecule that increases the half-life extension and/or a molecule that enables said peptide fragment to cross the blood-brain-barrier and/or at least one D-alanine at the N-terminus and/or the C-terminus.

In another embodiment, the invention provides a peptidomimetic generated from a peptide as depicted in SEQ ID NO: 1 or a homologue thereof of at least 95% amino acid identity for use as a medicament. In another embodiment, the invention provides a peptidomimetic generated from a peptide fragment derived from a peptide as depicted in SEQ ID NO: 1 or a homologue thereof of at least 95% amino acid identity, or from a peptide as depicted in SEQ ID NO: 2 or a homologue thereof of at least 95% amino acid identity or as depicted in SEQ ID NO: 3 or a homologue thereof of at least 95% amino acid identity for use as a medicament. In particular embodiments, said peptidomimetic for use as a medicament further comprises a molecule that increases the half-life extension. In other particular embodiments, said peptidomimetic for use as a medicament further comprises a molecule that enables said peptidomimetic to cross the blood-brain-barrier. In other particular embodiment, said peptidomimetic for use as a medicament further comprises at least one D-alanine at the N-terminus and/or the C-terminus. In other embodiments, said peptidomimetic for use as a medicament further comprises a molecule that increases the half-life extension and/or a molecule that enables said peptidomimetic to cross the blood-brain-barrier and/or at least one D-alanine at the N-terminus and/or the C-terminus.

In another embodiment, peptides, peptidomimetics and antibodies according to the invention comprising a cell penetrant carrier are used as a medicament. Said medicament is needed in a therapeutically effective amount. One of ordinary skill in the art will recognize that the potency and, therefore, an "effective amount" can vary for the inhibitory agents of the present invention. One skilled in the art can readily assess the potency of the inhibitory agent. A medicament to prevent and/or to treat an individual with a neurological and/or psychiatric disorder, relates to a composition comprising agents as described in the application present and a pharmaceutically acceptable carrier or excipient (both terms can be used interchangeably) to treat or to prevent neurological and psychiatric disorders, such as cognitive impairments, anxiety, depression, epilepsy, dystonia, neuropathic pain, narcolepsy or spasticity, as described herein.

In a ninth aspect, the application provides a peptide as depicted in SEQ ID NO: 1 or a homologue thereof of at least 95% amino acid identity for use to treat cognitive impairments, anxiety, depression, epilepsy, dystonia, neuropathic pain, narcolepsy or spasticity.

Peptides, peptidomimetics and antibodies according to the invention can be useful to treat any neurological disorder. Neurological disorders are diseases of the central and peripheral nervous system comprising the brain, spinal cord, cranial nerves, peripheral nerves, nerve roots, autonomic nervous system, neuromuscular junction, or muscles. These disorders comprise epilepsy, Alzheimer disease and other dementias, cerebrovascular diseases including stroke, migraine and other headache disorders, multiple sclerosis, Parkinson's disease, neuroinfections, brain tumours, traumatic disorders of the nervous system due to head trauma, and neurological disorders as a result of malnutrition.

Peptides, peptidomimetics and antibodies of the application can be used to treat psychiatric disorders. Psychiatric disorders comprise a broad range of problems, with different symptoms.

However, they are generally characterized by some combination of abnormal thoughts, emotions, behaviour and relationships with others. A non-limiting list of examples comprises schizophrenia, depression, intellectual disabilities and disorders due to drug abuse.

The above given list of disorders is a non-limiting list which does not limit the present application.

In another embodiment, the invention provides a peptide fragment derived from a peptide as depicted in SEQ ID NO: 1 or a homologue thereof of at least 95% amino acid identity, said peptide fragment is depicted in SEQ ID NO: 2 or a homologue thereof of at least 95% amino acid identity, or depicted in SEQ ID NO: 3 or a homologue thereof of at least 95% amino acid identity for use to treat cognitive impairments, anxiety, depression, epilepsy, dystonia, neuropathic pain, narcolepsy or spasticity. In one particular embodiment, said peptide fragment for use to treat cognitive impairments, anxiety, depression, epilepsy, dystonia, neuropathic pain, narcolepsy or spasticity further comprises a molecule that increases the half-life extension. In another particular embodiment, said peptide fragment for use to treat cognitive impairments, anxiety, depression, epilepsy, dystonia, neuropathic pain, narcolepsy or spasticity further comprises a molecule that enables said peptide fragment to cross the blood-brain-barrier. In another particular embodiment, said peptide fragment for use to treat cognitive impairments, anxiety, depression, epilepsy, dystonia, neuropathic pain, narcolepsy or spasticity further comprises at least one D-alanine at the N-terminus and/or the C-terminus. In another embodiment, said peptide fragment for use to treat cognitive impairments, anxiety, depression, epilepsy, dystonia, neuropathic pain, narcolepsy or spasticity further comprises a molecule that increases the half-life extension and/or a molecule that enables said peptide fragment to cross the blood-brain-barrier and/or at least one D-alanine at the N-terminus and/or the C-terminus.

In another embodiment, the invention provides a peptidomimetic generated from a peptide as depicted in SEQ ID NO: 1 or a homologue thereof of at least 95% amino acid identity for use to treat cognitive impairments, anxiety, depression, epilepsy, dystonia, neuropathic pain, narcolepsy or spasticity. In another embodiment, the invention provides a peptidomimetic generated from a peptide fragment derived from a peptide as depicted in SEQ ID NO: 1 or a homologue thereof of at least 95% amino acid identity, or from a peptide as depicted in SEQ ID NO: 2 or a homologue thereof of at least 95% amino acid identity or as depicted in SEQ ID NO: 3 or a homologue thereof of at least 95% amino acid identity for use to treat cognitive impairments, anxiety, depression, epilepsy, dystonia, neuropathic pain, narcolepsy or spasticity. In particular embodiments, said peptidomimetic for use to treat cognitive impairments, anxiety, depression, epilepsy, dystonia, neuropathic pain, narcolepsy or spasticity further comprises a molecule that increases the half-life extension. In other particular embodiments, said peptidomimetic for use to treat cognitive impairments, anxiety, depression, epilepsy, dystonia, neuropathic pain, narcolepsy or spasticity further comprises a molecule that enables said peptidomimetic to cross the blood-brain-barrier. In other particular embodiment, said peptidomimetic for use to treat cognitive impairments, anxiety, depression, epilepsy, dystonia, neuropathic pain, narcolepsy or spasticity further comprises at least one D-alanine at the N-terminus and/or the C-terminus. In other embodiments, said peptidomimetic for use to treat cognitive impairments, anxiety, depression, epilepsy, dystonia, neuropathic pain, narcolepsy or spasticity further comprises a molecule that increases the half-life extension and/or a molecule that enables said peptidomimetic to cross the blood-brain-barrier and/or at least one D-alanine at the N-terminus and/or the C-terminus.

In a tenth aspect, the application provides an antibody specifically binding to the sushi domain 1 of the $GABA_B1a$ receptor. The amino acid sequence of sushi domain 1 of the human $GABA_B1a$ receptor is depicted in SEQ ID NO: 5.

```
SEQ ID NO: 5: Sushi domain 1 of the human GABA_B1a
receptor:
TSEGCQIIHPPWEGGIRYRGLTRDQVKAINFLPVDYEIEYVCRGEREVVG
PKVRKCLANGSWTDMDTPSRCV
```

Also envisaged by the term "antibody" are antibody derivatives referring to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments, such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

In yet another embodiment the invention provides an antibody against the extension domain of sAPPα. This is equivalent as saying that an antibody is provided specifically binding to SEQ ID NO: 1 or a homologue thereof of at least 95% amino acid identity. In a particular embodiment the invention provides an antibody specifically binding to SEQ ID NO: 1 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity. In another particular embodiment the invention provides an antibody specifically binding to a sequence fragment derived from SEQ ID NO: 1 or a homologue thereof of at least 95% amino acid identity, said sequence fragment is depicted in SEQ ID NO: 2, or a homologue thereof of at least 95% amino acid identity, or depicted in SEQ ID NO: 3 or a homologue thereof of at least 95% amino acid identity. In particular embodiments, an antibody specifically binding to a sequence fragment derived from SEQ ID NO: 1 or a homologue thereof of at least 95% amino acid identity, said sequence fragment is depicted in SEQ ID NO: 2 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity, or depicted in SEQ ID NO: 3 or a homologue thereof of at least 99%, 98%, 97%, 96, 95%, 94%, 93%, 92%, 91%, 90%, 89%, 88%, 87%, 86%, 85%, 84%, 83%, 82%, 81%, or 80% amino acid identity is provided. In particular embodiments, said antibody comprises an element to cross the blood brain barrier. In more particular embodiments, said antibody comprises an element increases the half-life of said antibody. In yet another particular embodiment, said antibody is provided for use as a medicament. In a more particular embodiment, said antibody is provided for use to treat cognitive impairments, anxiety, depression, epilepsy, dystonia, neuropathic pain, narcolepsy or spasticity. In an even more particular embodiment, said antibody is a single domain antibody or even more particular a VHH or a nanobody. According to particular embodiments, a pharmaceutical composition is provided comprising said antibody, or single domain antibody, or VHH or nanobody and a pharmaceutically acceptable carrier.

In another aspect, the application provides an antibody specifically binding to the sushi domain 1 of the $GABA_B1a$ receptor. In a particular embodiment, said sushi domain 1 is the peptide depicted in SEQ ID NO: 5. In another embodiment, said antibody specifically binding to the sushi domain 1 of the $GABA_B1a$ a receptor comprises an element to cross the blood brain barrier and/or an element that increases the half-life of said antibody. In a particular embodiment, said antibody against said sushi domain is provided for use as a medicament or more particularly for use to treat cognitive impairments, anxiety, depression, epilepsy, dystonia, neuropathic pain, narcolepsy or spasticity. In an even more particular embodiment, said antibody against said sushi domain is a single domain antibody or even more particular a VHH or a nanobody. According to particular embodiments, a pharmaceutical composition is provided comprising above described antibody, or single domain antibody, or VHH or nanobody and a pharmaceutically acceptable carrier.

In a twelfth aspect, a method to produce or identify a compound which can modulate the activity of the $GABA_B$a receptor is provided, said method comprises the following steps:
  a. Providing a cell expressing a functional $GABA_B1a$ receptor,
  b. Administering a test compound to said cell,
  c. Monitoring the activity of said receptor and identifying a compound which modulates the activity of said receptor, wherein under the same conditions in the same cell without the test compound, a difference in the activity of said receptor identifies a test compound.

Also, a method is provided to produce or identify a compound which can modulate the activity of the $GABA_B$a receptor through binding to the sushi domain 1 of $GABA_B R1a$, said method comprises the following steps:
  a. Providing a cell expressing a functional $GABA_B1a$ receptor,
  b. Administering a test compound to said cell,
  c. Monitoring the activity of said receptor and identifying a compound which modulates the activity of said receptor, wherein under the same conditions in the same cell without the test compound, a difference in the activity of said receptor identifies a test compound.

Assays can be performed in an in vitro system. Therefore, in one embodiment, said cell expressing a functional $GABA_B1a$ receptor is an in vitro system comprising neuronal cells expressing a functional $GABA_B1a$ receptor. Neuronal cells or neurons are a type of cell in the central nervous system, which receive, integrate, and pass along information by releasing neurotransmitters. Said neurotransmitters are chemicals that cross-over from the terminal button at the end of an axon over the synapse to the neighbouring neuron. Non-limiting examples of neuron cells are primary cortical neurons, primary basal forebrain cholinergic neurons, primary neural stem cells, sensory neurons (e.g. retinal cells, olfactory epithelium cells), motor neurons (e.g. spinal motor neurons, pyramidal neurons, Purkinje cells) and interneurons (e.g. dorsal root ganglia cells).

In another embodiment, said cell expressing a functional $GABA_B$a receptor is selected from a recombinant cell, a neuronal cell or a primary neuron. In a particular embodiment, said cell expressing a functional $GABA_B1a$ receptor is a neuron present in an acute brain slice derived from a non-human mammal.

In more particular embodiments, said activity monitoring of the $GABA_B1a$ receptor is done via calcium release measuring, synaptic transmission measuring and cAMP.

In particular embodiments of the twelfth aspect and of its embodiments, said compound modulating the activity of the $GABA_B1a$ receptor, is a compound that increases the activity of said receptor. In most particular embodiments, said compounds increases the activity of said $GABA_B1a$ receptor with at least 10%, at least 25%, at least 50%, at least 75%, at least 100%, at least 2-fold, at least 5-fold or at least 10-fold. In other particular embodiments of the twelfth aspect and of its embodiments, said compound modulating the activity of the $GABA_B$a receptor, is a compound that decreased the activity of said receptor. In most particular embodiments, said compounds decreases the activity of said $GABA_B$a receptor with at least 10%, at least 25%, at least 50%, at least 75%, at least 100%, at least 2-fold, at least 5-fold or at least 10-fold.

Compounds tested in the screening method of the present application are not limited to a specific type of a compound. In one embodiment, entire compound libraries are screened. Compound libraries are a large collection of stored compounds utilized for high throughput screening. Compounds in a compound library can have no relation to one another, or alternatively have a common characteristic. For example, a hypothetical compound library may contain all known compounds known to bind to a specific binding region. As would be understood by one skilled in the art, the methods of the application are not limited to the types of compound libraries screened. For high-content screening, compound libraries may be used. Examples include, but are not limited to, natural compound libraries, allosteric compound libraries, peptide libraries, antibody fragment libraries, synthetic compound libraries, etc. In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds identified can serve as conventional "hit compounds" or can themselves be used as potential or actual therapeutics.

In specific embodiments, immune-based assays are comprised in steps a) and/or c) of the claimed method, more specifically "immune-based assays" or "immune-based detection" for monitoring the expression of a functional $GABA_B1a$ receptor and/or monitoring the activity of said receptor in a method for producing or identifying a compound that impairs the activity of said receptor.

In said embodiments, "immune-based assays" comprise the most broadly used bio-detection technologies that are based on the use of antibodies, and are well known in the art. Antibodies are highly suited for detecting small quantities of target proteins in the presence of complex mixtures of proteins. As used herein, an "immune-based assay", "immunoassay" or "immune-based detection" (each of these terms can be used interchangeably) refers to a biochemical binding assay involving binding between antibodies and antigen, which measures the presence or concentration of a substance in a sample, such as a biological sample, using the reaction of an antibody to its cognate antigen, for example the specific binding of an antibody to a protein. Both the presence of the antigen or the amount of the antigen present can be measured.

Examples of immunoassays are enzyme linked immunosorbent assays (ELISAs), enzyme linked immunospot assay (ELISPOT), immunobead capture assays, Western blotting, gel-shift assays, protein arrays, multiplexed bead arrays, magnetic capture, fluorescence resonance energy transfer (FRET), a sandwich assay, a competitive assay, an immunoassay using a biosensor, an immunoprecipitation assay etc. Examples of assays which can require these detection methods for producing compounds in the context of the present invention are described in the Example section, without the purpose of being limitative. It should be clear to the skilled artisan that the present screening methods might be based on a combination or a series of measurements, particularly when establishing the link between the impairment of the activity of the $GABA_B1a$ receptor by specific test compounds. Also, it should be clear that there is no specific order in performing these measurements while practicing the present invention.

In general, immune-based assays involve contacting a sample suspected of containing a molecule of interest (such as the test compound) with an antibody to the molecule of interest or contacting an antibody to a molecule of interest (such as antibodies to sushi domain 1 of $GABA_B1a$) with a molecule that can be bound by the antibody, as the case may be, under conditions effective to allow the formation of immune complexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest in a sample, which methods generally involve the detection or quantitation of any immune complexes formed during the binding process. In general, the immune-based detection is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immune-based detection methods and labels. As used herein, a label can include a fluorescent dye, a member of a binding pair, such as biotin/streptavidin, a metal (e.g., gold), or an epitope tag that can specifically interact with a molecule that can be detected, such as by producing a coloured substrate or fluorescence. Substances suitable for detectably labelling proteins include fluorescent dyes (also known herein as fluorochromes and fluorophores) and enzymes that react with colorimetric substrates (e.g., horseradish peroxidase). The use of fluorescent dyes is generally preferred in the practice of the invention as they can be detected at very low amounts. Furthermore, in the case where multiple antigens are reacted with a single array, each antigen can be labelled with a distinct fluorescent compound for simultaneous detection. Labelled spots on the array are detected using a fluorimeter, the presence of a signal indicating an antigen bound to a specific antibody. Fluorophores are compounds or molecules that luminesce. Typically, fluorophores absorb electromagnetic energy at one wavelength and emit electromagnetic energy at a second wavelength.

A variety of immunoassays can be used to detect one or more of the proteins disclosed or incorporated by reference herein. ELISA is a heterogeneous immunoassay, which can be used in the methods disclosed herein. The assay can be used to detect protein antigens in various formats.

In the "sandwich" format the antigen being assayed is held between two different antibodies. In this method, a solid surface is first coated with a solid phase antibody. The in vitro system composition comprises the antigen, to which the test compound is added, allows binding of the test compound, and therefore reduces the detection of the antigen via reaction with the bound antibody. Any unbound antigen is washed away. A known amount of enzyme-labelled antibody is then allowed to react with the bound antigen. Any excess unbound enzyme-linked antibody is washed away after the reaction. The substrate for the enzyme used in the assay is then added and the reaction between the substrate and the enzyme produces a colour change. The amount of visual colour change is a direct measurement of specific enzyme-conjugated bound antibody, and consequently the antigen present in the sample tested. ELISA can also be used as a competitive assay. In the competitive assay format, the test specimen containing the antigen to be determined is mixed with a precise amount of enzyme-labelled antigen and both compete for binding to an anti-antigen antibody attached to a solid surface. Excess free enzyme-labelled antigen is washed off before the substrate for the enzyme is added. The amount of colour intensity resulting from the enzyme-substrate interaction is a measure of the amount of antigen in the sample tested. A heterogeneous immunoassay, such as an ELISA, can be used to detect any of the proteins disclosed or incorporated by reference herein. In many immunoassays, as described elsewhere herein, detection of antigen is made with the use of antigens specific antibodies as detector molecules. However, immunoassays and the systems and methods of the present invention are not limited to the use of antibodies as detector molecules. Any substance that can bind or capture the antigen within a given sample may be used. Aside from antibodies, suitable substances that can also be used as detector molecules include but are not limited to enzymes, peptides, proteins, and nucleic acids. Further, there are many detection methods known in the art in which the captured antigen may be detected. In some assays, enzyme-linked antibodies produce a colour change. In other assays, detection of the captured antigen is made through detecting fluorescent, luminescent, chemiluminescent, or radioactive signals. The system and methods of the current invention is not limited to the particular types of detectable signals produced in an immunoassay.

In a thirteenth aspect, a method to produce or identify a compound is provided, wherein said compound modulates the activity of the $GABA_B1a$ receptor or wherein said compound modulated the activity of the $GABA_B a$ receptor through binding to the sushi domain 1 of said $GABA_B1a$ receptor, said method comprises the following steps:
  a. Providing a cell expressing a functional $GABA_B1a$ receptor,
  b. Administering a test compound to said cell,
  c. Identifying said test compound as a compound which modulates the activity of said $GABA_B1a$ receptor, if the activity of said receptor in the presence of said compound is statistically significantly different from the activity of said receptor in the absence of said test compound.

In one embodiment, said cell expressing a functional $GABA_B1a$ receptor is an in vitro system comprising neuronal cells expressing a functional $GABA_B1a$ receptor. In another embodiment, said cell expressing a functional $GABA_B1a$ receptor is selected from a recombinant cell, a neuronal cell or a primary neuron. In a particular embodiment, said cell expressing a functional $GABA_B1a$ receptor is a neuron present in an acute brain slice derived from a non-human mammal.

In more particular embodiments, the identification of said test compound is performed monitoring the activity of the $GABA_B a$ receptor, wherein said monitoring is done via calcium release measuring, synaptic transmission measuring and cAMP.

In particular embodiments of the thirteenth aspect and of its embodiments, said compound modulating the activity of the $GABA_B$ a receptor, is a compound that increases the activity of said receptor. In most particular embodiments, said compounds increases the activity of said $GABA_B$ aa receptor with at least 10%, at least 25%, at least 50%, at least 75%, at least 100%, at least 2-fold, at least 5-fold or at least 10-fold. In other particular embodiments of the thirteenth aspect and of its embodiments, said compound modulating the activity of the $GABA_B1a$ receptor, is a compound that decreased the activity of said receptor. In most particular embodiments, said compounds decreases the activity of said $GABA_B1a$ receptor with at least 10%, at least 25%, at least 50%, at least 75%, at least 100%, at least 2-fold, at least 5-fold or at least 10-fold.

The term "statistically significantly different" is well known by the person skilled in the art. Statistical significance plays a pivotal role in statistical hypothesis testing. It is used to determine whether the null hypothesis should be rejected or retained. The null hypothesis is the default assumption that nothing happened or changed. Regarding the above described thirteenth aspect, the null hypothesis is the default assumption that there is no difference in the activity of the $GABA_B1a$ receptor in the presence of said test compound compared to the activity of the $GABA_B1a$ receptor in the absence of said test compound. For the null hypothesis to be rejected, an observed result has to be statistically significant, i.e. the observed p-value is less than the pre-specified significance level a. The p-value of a result, p, is the probability of obtaining a result at least as extreme, given that the null hypothesis were true. The activity of the $GABA_B1a$ receptor in the presence of said test compound is statistically significantly different compared to the activity of the $GABA_B1a$ receptor in the absence of said test compound, when p<a. In one embodiment, $\alpha$ is 0.05. In a more particular embodiment, a is 0.01. In an even more particular embodiment, $\alpha$ is 0.001.

In a fourteenth aspect, a method to produce or identify an inhibitor of the sAPPα binding to the $GABA_B1a$ receptor, said method comprising:
  a. Measuring the induction of long-term potentiation by sAPPα or fragments thereof in cells expressing a functional $GABA_B1a$ receptor;
  b. Applying a test compound to said cells;
  c. Identifying said test compound as a compound that inhibits the sAPPα binding to the $GABA_B1a$ receptor if said test compound blocks said induction of the long-term potentiation by sAPPα.

In particular embodiments, said compound that inhibits the sAPPα binding to the $GABA_B1a$ receptor blocks said induction with at least 10%, at least 20%, at least 30%, at least 40%, at least 50%, at least 60%, at least 70%; at least 80%, at least 90%, or at least 95%.

"Long-term potentiation" or "LTP" as used herein is a persistent strengthening of synapses based on recent patterns of activity. These are patterns of synaptic activity that produce a long-lasting increase in signal transmission between two neurons. Long-term potentiation (LTP) is induced by stimulation of Schaffer collateral fibers and the response of CA1 pyramidal neurons is measured by extracellular recordings. For measuring antagonists, a primed burst stimulation protocol is used to activate $GABA_B R$ receptors. Under this protocol, an antagonist blocks induction of LTP. For measuring agonists, a non-primed high frequency stimulation protocol is used. Under this protocol, an agonist facilitates LTP.

In another aspect, a method to produce or identify an inhibitor of the sAPPα binding to the $GABA_B1a$ receptor, said method comprising:
  a. Measuring the reduction in EPSC frequency and/or IPSC frequency by sAPPα or fragments thereof in cells expressing a functional $GABA_B1a$ receptor;
  b. Applying a test compound to said cells;
  c. Identifying said test compound as a compound that inhibits the sAPPα binding to the $GABA_B1a$ receptor if said test compound blocks said reduction in EPSC frequency or IPSC frequency by sAPPα.

In one embodiment, said EPSC is mEPSC and said IPSC is mIPSC. In particular embodiments, said compound that inhibits the sAPPα binding to the $GABA_B1a$ receptor blocks said reduction with at least 10%, at least 20%, at least 30%, at least 40%, at least 50%, at least 60%, at least 70%; at least 80%, at least 90%, or at least 95%.

Excitatory postsynaptic currents (EPSC) or miniature EPSC (mEPSC) and inhibitory postsynaptic currents (IPSC) or miniature IPSC (mIPSC) are known by the person skilled in the art of neuroscience. mEPSCs and mIPSCs can be measured in cultured primary hippocampal neurons.

In particular embodiments of the fourteenth aspect and of its embodiments, said fragments thereof (i.e. fragments of sAPPα) are any of the peptides of the application, or any of the peptide fragments of the application or any of the peptidomimetics of the application or any of the molecules of the application.

In other particular embodiments of the fourteenth aspect and of its embodiments, said cell expressing a functional GABA$_B$1a receptor is an in vitro system comprising neuronal cells expressing a functional GABA$_B$1a receptor. In another embodiment, said cell expressing a functional GABA$_B$1a receptor is selected from a recombinant cell, a neuronal cell or a primary neuron. In a particular embodiment, said cell expressing a functional GABA$_B$1a receptor is a neuron present in an acute brain slice derived from a non-human mammal. In more particular embodiments, the identification of said test compound is performed monitoring the activity of the GABA$_B$1a receptor, wherein said monitoring is done via calcium release measuring, synaptic transmission measuring and cAMP.

The various aspects of the invention are further described by the following examples, which are not intended to limit the invention in any manner. It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1

Identification of APP as Binding Partner of Sushi Domain 1 of the GABA$_B$1a Receptor Enrichment of APP at presynaptic terminals was determined through biochemical fractionation and super-resolution microscopy. APP and its family members, APP-like protein 1 (APLP1) and APP-like protein 2 (APLP2), were enriched in the synaptic fraction compared to the crude membrane fraction (FIG. 1E). Further, APP and the APLPs were strongly enriched in the Triton-soluble fraction containing the presynaptic protein synaptophysin (Syp), and were largely absent in the postsynaptic protein-containing Triton-insoluble fraction where the postsynaptic density protein 95 (PSD-95) and the NR2A subunit of the NMDA receptor are found (FIG. 1E). Using super-resolution structured illumination microscopy, we found that APP co-localized with excitatory and inhibitory presynaptic markers (vesicular glutamate transporter 1 (VGLUT1) and vesicular GABA transporter (VGAT), respectively), but not with excitatory and inhibitory postsynaptic markers (PSD-95 and gephyrin, respectively), in the mouse hippocampal CA1 region (FIG. 1F). Together, our data indicate that APP is enriched at presynaptic terminals of excitatory and inhibitory synapses.

Next, we aimed to identify synaptic binding partners for the APP ectodomain at the cell surface and performed an unbiased shotgun proteomics screen using sAPPα-Fc as bait and synaptosome extracts as prey. We performed the screen as described in Savas et al., Nature Protocols, 2014. sAPP coupled to an Fc fragment (sAPPα-Fc) was expressed and purified from HEK293 cells, was coupled to protein G sepharose beads and incubated with synaptosome extracts, prepared from rat whole brain, for batch binding. The sAPPα-Fc baits with bound prey from synaptosome extracts was then captured, washed, and eluted. The purified material was digested to peptides and analyzed by multidimensional liquid chromatographic tandem mass spectrometry (LCLC-MSMS). Bioinformatics was performed to exclude any proteins found in Fc control and to include only proteins with predicted transmembrane domains. From three experimental repeats of the screen, the GABA$_B$ Receptor was the top cell-surface protein identified with a summed peptide count of 35 and a summed spectra count of 22.

Example 2

Identification of the 33 Aa Domain in APP and of the 72 Aa Domain in the GABA$_B$R To confirm the APPα-GABA$_B$R interaction and identify the interacting domains, we used a cell-based binding assay. Purified Fc-sAPPα (or its domains) were exogenously applied to GABA$_B$R-transfected HEK293 cells. Bound Fc-sAPPα was determined by immunofluorescence.

Figure 2:
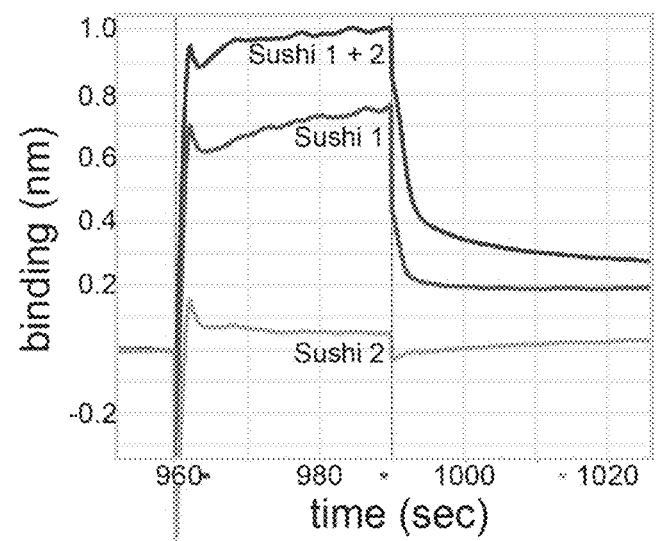
FIG. 2: Sushi 1 of GABA$_B$R1a is sufficient to bind sAPPα. A. Using BioLayer Interferometry we demonstrated direct binding of sAPPα to the sushi domains in GABA$_B$R1a and that the sushi 1 domain (72 aa) is sufficient for binding sAPPα. B. Binding of purified sushi 1 domain and sAPPα proteins by ITC.
Figure 2:
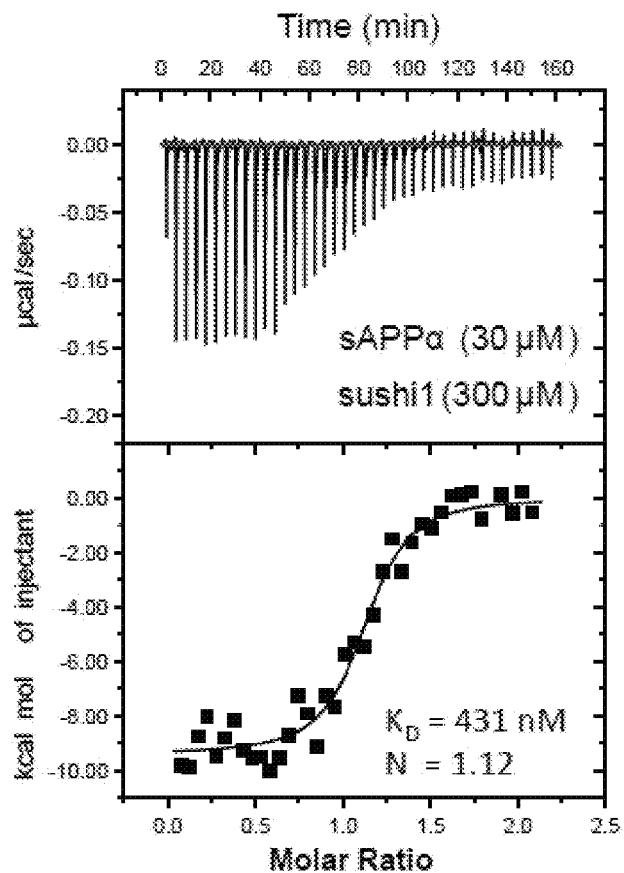

We first determined which GABA$_B$ subunit and isoform sAPPα bound. The GABA$_B$R is comprised of two subunits, the GABA$_B$R1 and the GABA$_B$R2 subunit. GABA$_B$R1 is present as two main isoforms (1a and 1b), with the only difference between these isoforms being the presence of two protein-binding sushi repeats in the ectodomain of GABA$_B$R1a (FIG. 1A-B). We found that Fc-sAPPα only interacts with GABA$_B$R1a which suggests that the sushi domains in GABA$_B$R1a mediate its binding to the APP ectodomain (FIG. 1C-D). Using BioLayer Interferometry we demonstrated direct binding and that the Sushi 1 domain (72 aa) is sufficient for binding sAPPα (FIG. 2A) and using isothermal titration calorimetry (ITC) we determined that the dissociation constant (KD) is 431 nM (FIG. 2B). These data show that sAPPα binds directly and selectively to the sushi1 domain of GABABR1a with sub-micromolar affinity. The sequence of the Sushi domain 1 is TSEGCQIIHPP-WEGGIRYRGLTRDQVKAINFLPVDYEIEY VCRG-EREVVGPKVRKCLANGSWTDMDTPSRCV.

Figure 3:
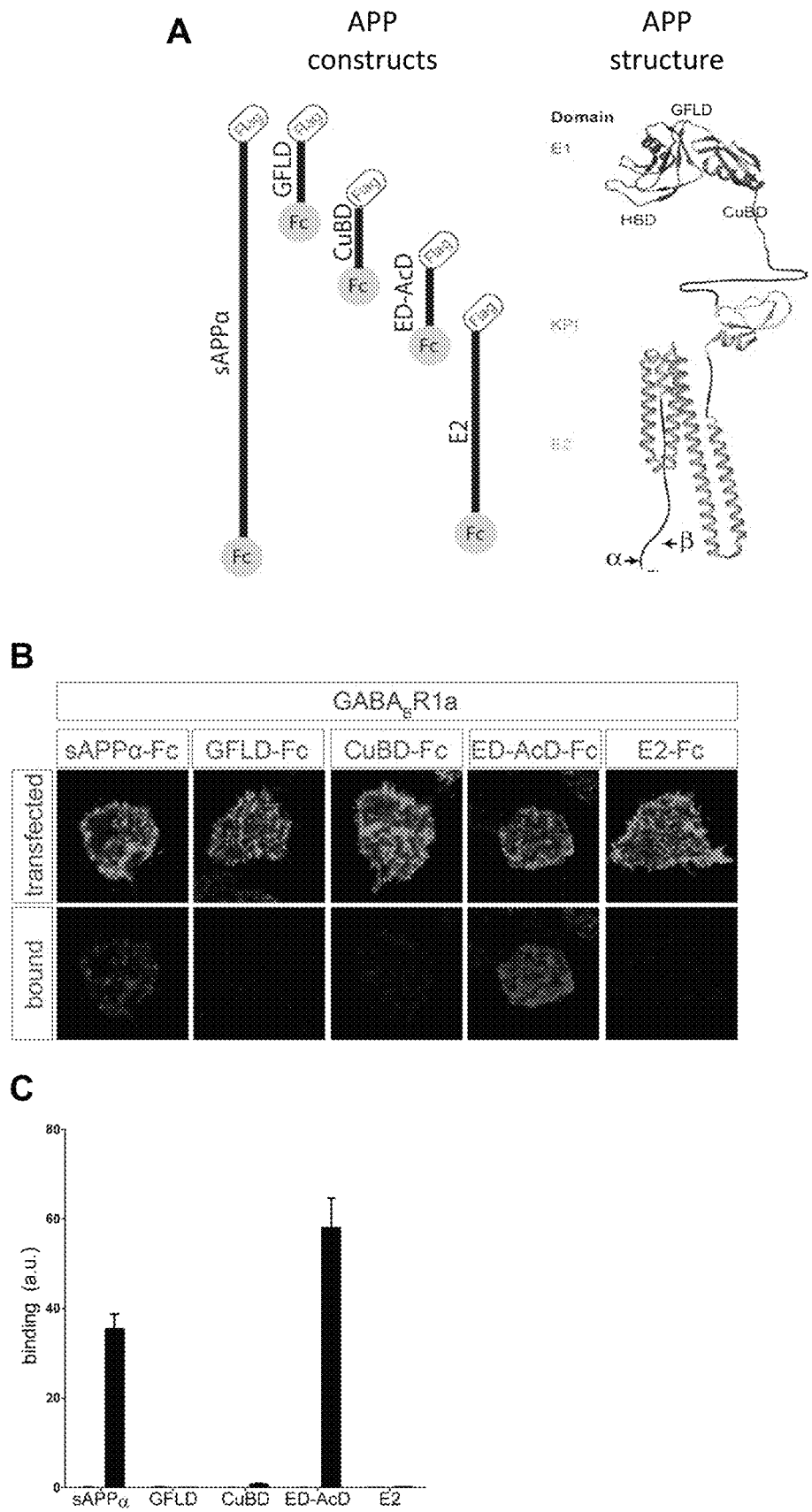
FIG. 3: Binding of the Fc-proteins of the various APPα domains detected by immunofluorescence. A. Schematic representation of the different sAPPα domains, APP construct and APPα structure. B-C. Confocal images (Bb) and quantifications (C) of immunostaining for sAPPα-Fc, GFLD-Fc, CuBD-Fc, ED-AcD-Fc, or E2-Fc (red) binding to GFP- or GABA$_B$R1a-expressing HEK293 cells (green) (n=16-32). We did not detect binding of the growth factor like domain (GFLD), Copper binding domain (CuBD), or E2 domain while interaction of the extension domain-acidic region (ED-AcD) of APPα with GABA$_B$R1a was demonstrated.
Figure 4:
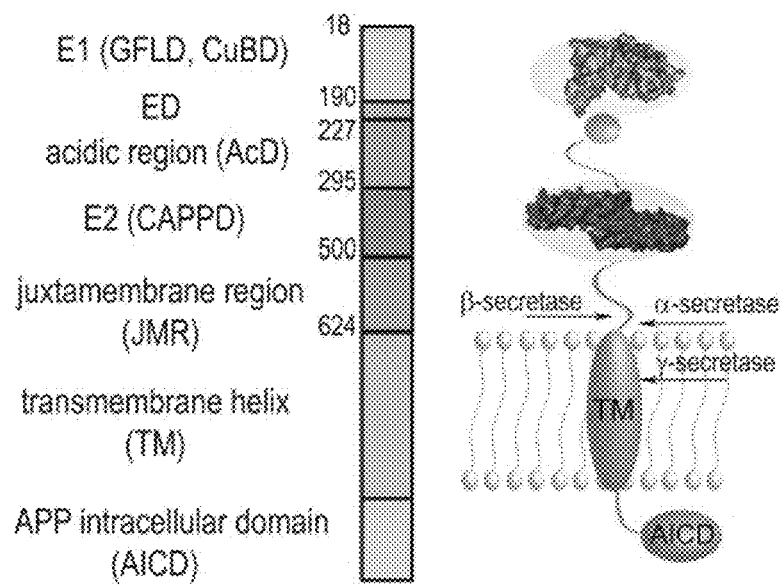
FIG. 4: Binding affinity of the different APPα domains to GABA$_B$R1a. A. Schematic representation of the different sAPPα domains. B-C Confocal images (B) and quantifications (C) of immunostaining for sAPPα ED-AcD-Fc, ED-Fc or AcD-Fc (red) binding to GFP- or GABA$_B$R1a expressing HEK293 cells (green) (n=14-16). The extension domain-acidic region (ED-AcD) of APPα shows the highest interaction.
Figure 4:
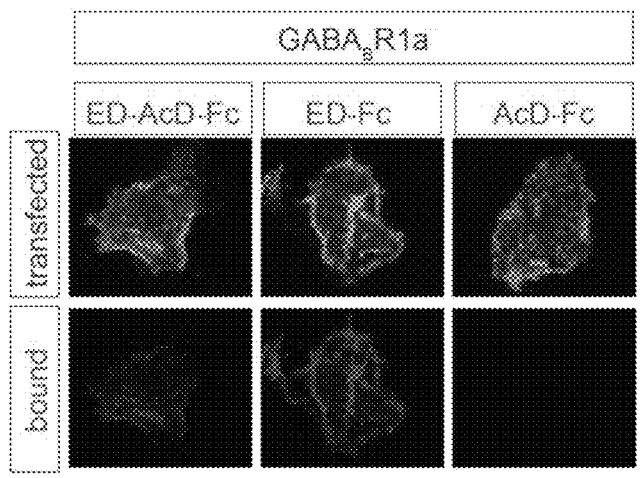
Figure 4:
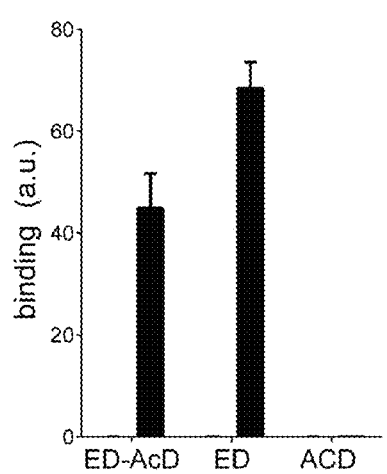
Figure 5:
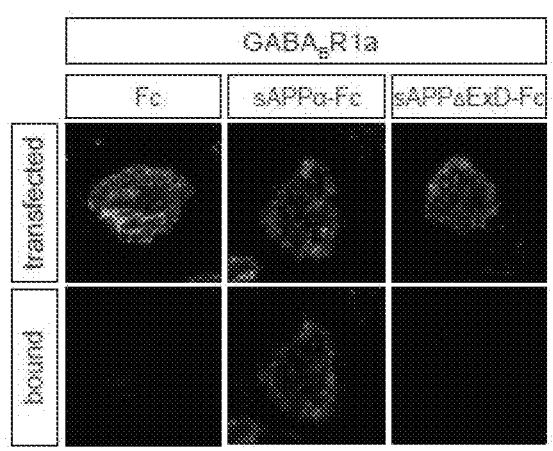
FIG. 5: The extension domain (ED or ExD) of APPα specifically interacts with GABA$_B$R1a. A-B Confocal images (A) and quantifications (B) of immunostaining for sAPPα-Fc or sAPPαΔExD-Fc (red) binding to GFP- or GABA$_B$R1a-expressing HEK293 cells (green) (n=26). The 33 aa extension domain was sufficient for binding.
Figure 5:
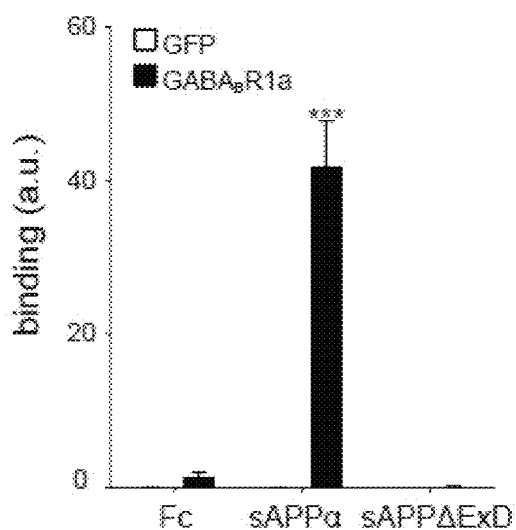

To narrow down the binding site within APPα, we generated Fc-fusion proteins for the various APPa domains (FIG. 3A). We did not detect binding of the growth factor like domain (GFLD), Copper binding domain (CuBD), Acidic domain (AcD), or E2 domain (FIG. 3B-C, FIG. 4B-C). Instead we found that the 33 aa extension domain (ED) was sufficient for binding to GABA$_B$R1a (FIG. 4B-C, FIG. 5A-B). The sequence of the extension domain is NVDSADAEEDDSDVWWGGADTDYADGSEDKVVE.

Example 3

Restriction of the Binding Domain in APP

Figure 6:
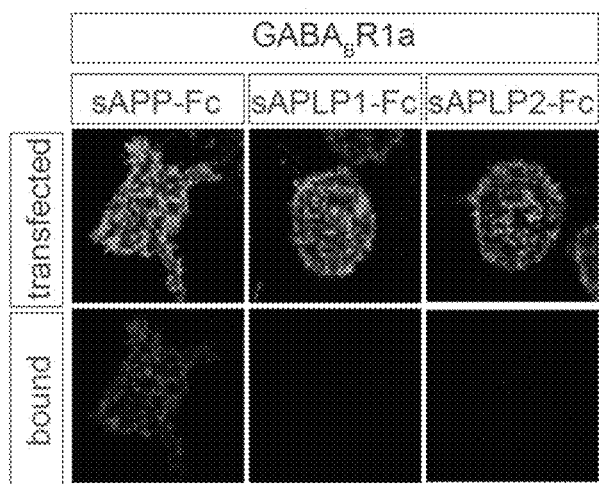
FIG. 6: APPα but not its family members specifically interacts with GABA$_B$R1a. A-B. Confocal images (A) and quantifications (B) of immunostaining for sAPPα-Fc, sAPLP1-Fc, of sAPLP2-Fc (red) binding to GFP or GABA$_B$R1a expressing HEK293 cells (green) (n=24). C. Sequence alignment of APP, APLP1 and APLP2. D. Sequence alignment for the extension domain of human APPα with APLPs and with 7 vertebrate APPα sequences.
Figure 6:
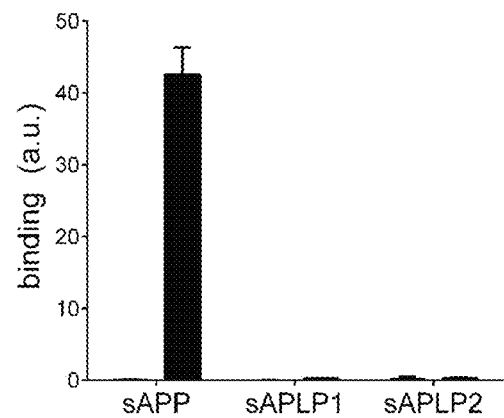

We found that GABA$_B$R1a specifically interacts with APPα but not with its family members (FIG. 6A-B). The specific binding domain within the APPα extension domain (APP ExD or APP ED) is further narrowed down to sequence DDSDVWWGGADTDYADG. The APP ExD is not conserved in APLP1 and APLP2 (FIG. 6C-D) and, accordingly, sAPLP1-Fc and sAPLP2-Fc fail to bind GABA$_B$R1a-expressing cells (FIG. 6A-B). The ExD-AcD (FIG. 7A) fragment has similar binding affinity as sAPPα (FIG. 2B) in ITC experiments at an approximate molar ratio of 1. The two Trp residues and the DYAD motive are shown to mediate protein-peptide interaction. The flanking regions of the extension domain are low complexity regions not prominent in a specific protein-peptide interaction.

Figure 7:
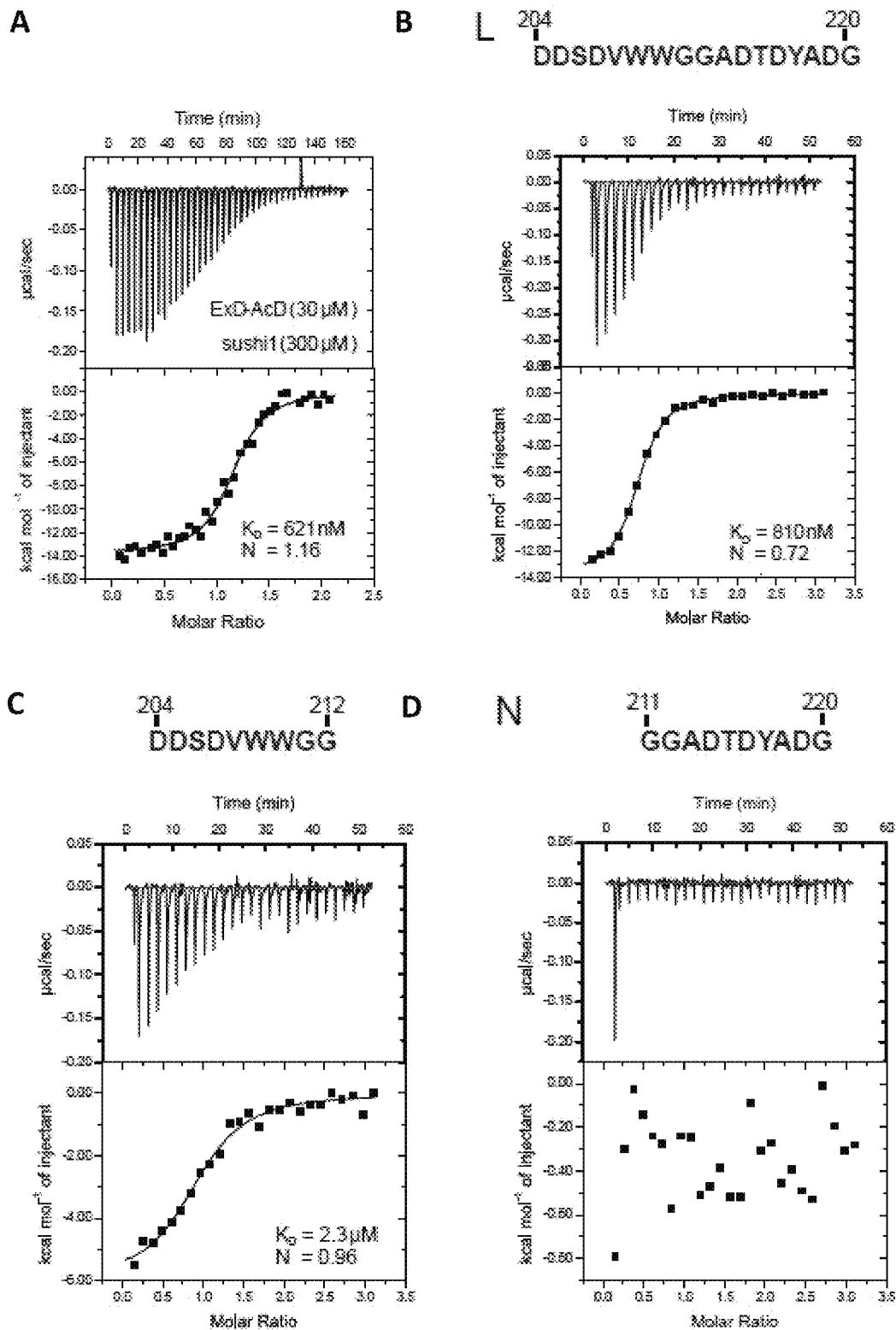
FIG. 7. A. Binding of purified sushi1 and sAPPα proteins by ITC. B-D. ITC binding experiments of purified sushi1 and synthetic peptides within the ExD corresponding (B) 204-220AA (C) 204-212AA, or (D) 211-220AA of APP695. (Error bars represent s.e.m. The number of cells from 2-4 independent experiments is defined by n. Two-way ANOVA with Bonferroni's post hoc analysis; ***P<0.001).

Alignment of the APP ExD from 7 vertebrate species reveals the strongest conservation within a 17AA stretch (FIG. 6D). This synthetic 17mer peptide binds sushi1 of $GABA_BR1$ with a KD of 810 nM (Figure B) similar to the binding affinity of the entire linker region (FIG. 7A). Shortening the peptide to APP695 residues 204-212 lowers the KD to 2.3 µM (FIG. 7C); whereas residues 211-220 fails to bind (FIG. 7D). Thus, a conserved 17AA sequence within the sAPP ExD is sufficient for direct binding to the sushi1 domain of $GABA_BR1a$.

Example 4

Figure 8:
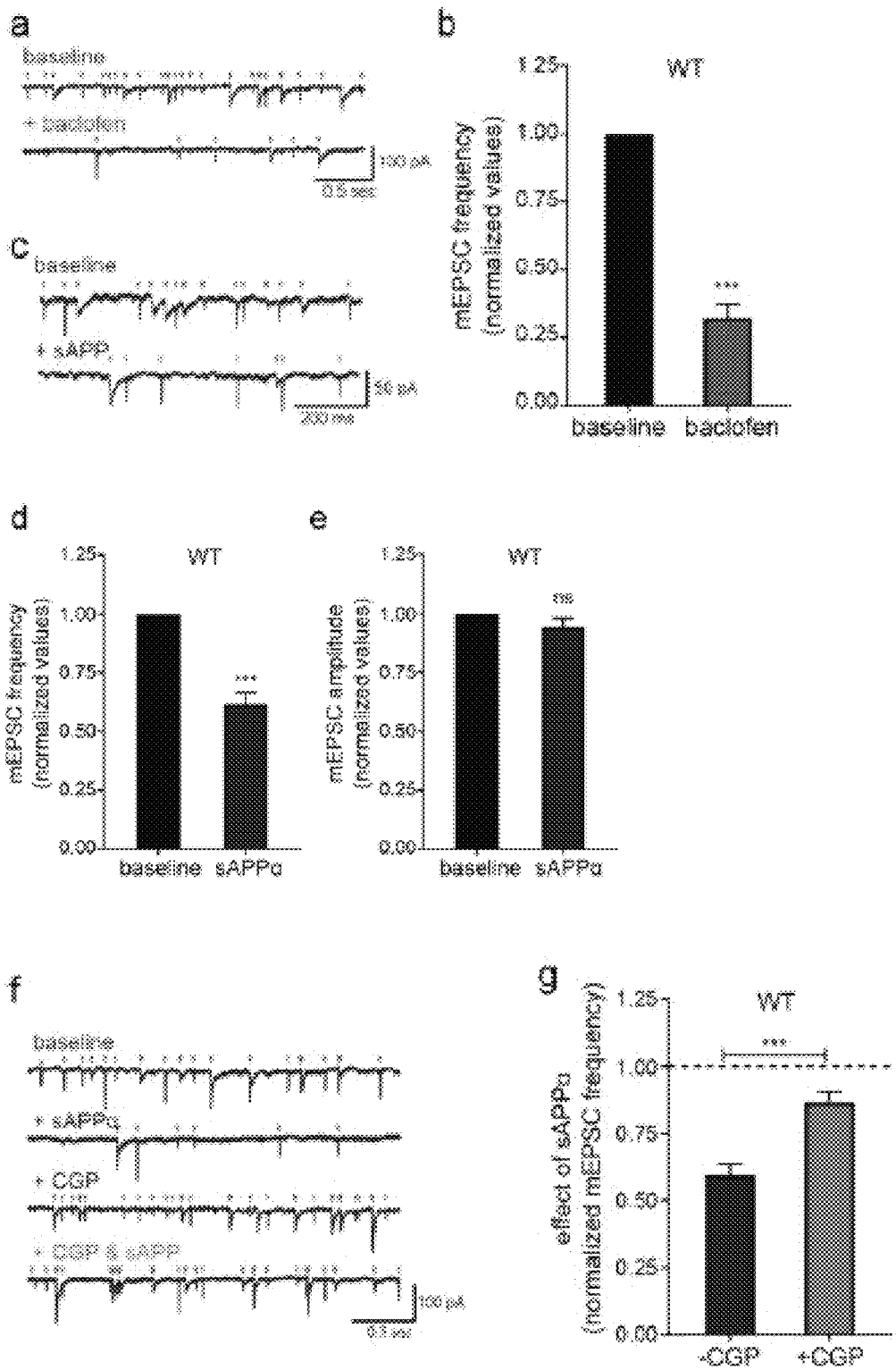
FIG. 8. sAPPα reduces presynaptic release via GABA$_B$Rs in cultured hippocampal neurons. a,b, Example traces of mEPSCs (green arrowheads) and mIPSCs (red arrowheads) (a) and average mEPSC frequency normalized to baseline (b) recorded from wild type neurons before (baseline) and after treatment with baclofen, a GABA$_B$R agonist. (n=12, paired t-test). c-e, Example traces of mEPSCs (green arrowheads) and mIPSCs (red arrowheads) (c) and average mEPSC frequency (d) and amplitude (e) normalized to baseline recorded from wild type neurons before (baseline) and after treatment with sAPPa. (n=13, paired t-test). f,g, Example traces of mEPSCs (green arrowheads) and mIPSCs (red arrowheads) (f) and quantification of the effect of sAPPα on mEPSC frequency normalized to baseline (g) either without (blue) or with (green) preincubation with CGP55845 (CGP), a GABA$_B$R antagonist. Dotted line denotes baseline. (n=14-17, unpaired t-test). h,i, Example traces of mEPSCs (green arrowheads) and mIPSCs (red arrowheads) and average mEPSC frequency normalized to baseline (i) recorded from wildtype neurons before (baseline) and after treatment with either sAPPα ExD-AcD, 17mer (APP695 204-220AA), sAPPαΔExD, or sAPLP1. (n=17-20, one way ANOVA with Dunnett's post hoc analysis). j,k, Average mEPSC frequency normalized to baseline recorded from App/Aplp1 dKO primary hippocampal neurons before (baseline) and after treatment with either sAPPα (j) or baclofen (k). Dotted line denotes effect in wildtype neurons. (n=14, paired t-test). 1, High-magnification ΔF images before and after application of 1 μM sAPPα. m,n, Representative ΔF histograms before (control, Cnt) and after either sAPPα (in) or sAPPαΔED (n) application. o, Summary of the dose-dependent inhibitory effect of sAPPα on the presynaptic vesicle recycling (S, normalized to Cnt). (N=5-8, one way ANOVA analysis with post hoc Tukey's analysis). p, High-magnification ΔF images before and after application of sAPPα in the presence of a GABA$_B$R antagonist, CGP54626 (CGP). q, Representative ΔF histograms before and after application of 1 μM sAPPα in the presence of CGP. r, Summary of sAPPα effect on presynaptic vesicle recycling in hippocampal neurons with (N=8) or without (N=8) CGP (normalized to Cnt). (Error bars represent s.e.m. The number of neurons is defined as n29 from 2 (b,k) or 3 (d,e,g,I,j) independent experiments. The number of experiments is defined by N (o,r). ***P≤0.001).
Figure 8:
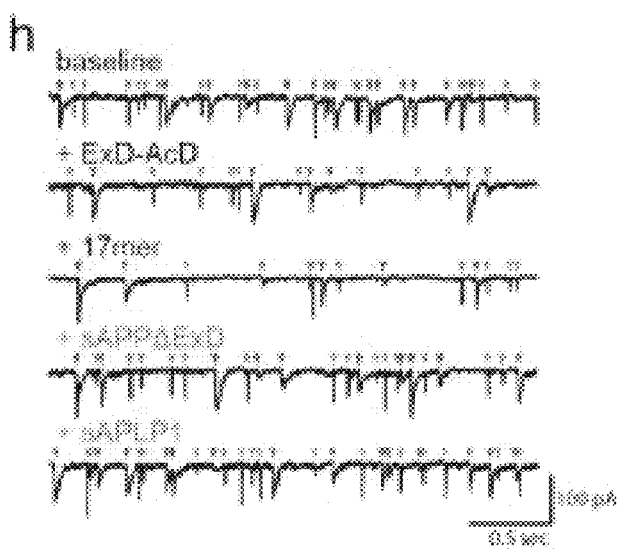
Figure 8:
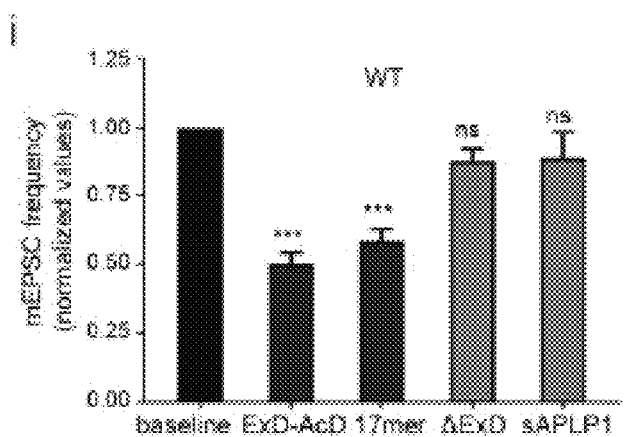
Figure 8:
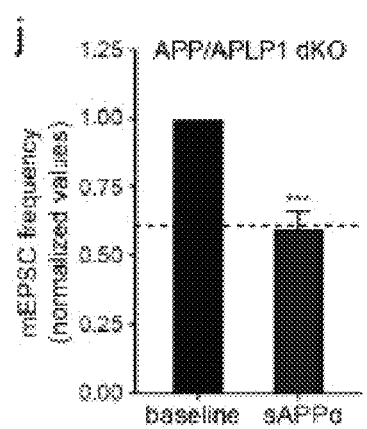
Figure 8:
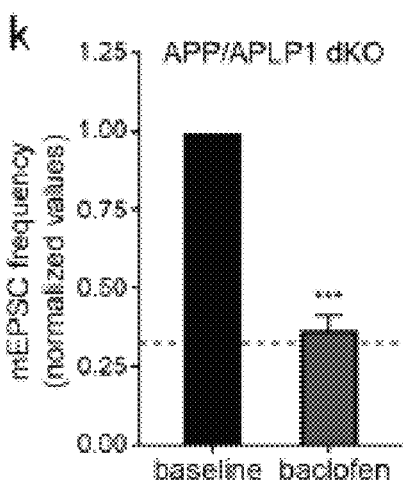
Figure 8:
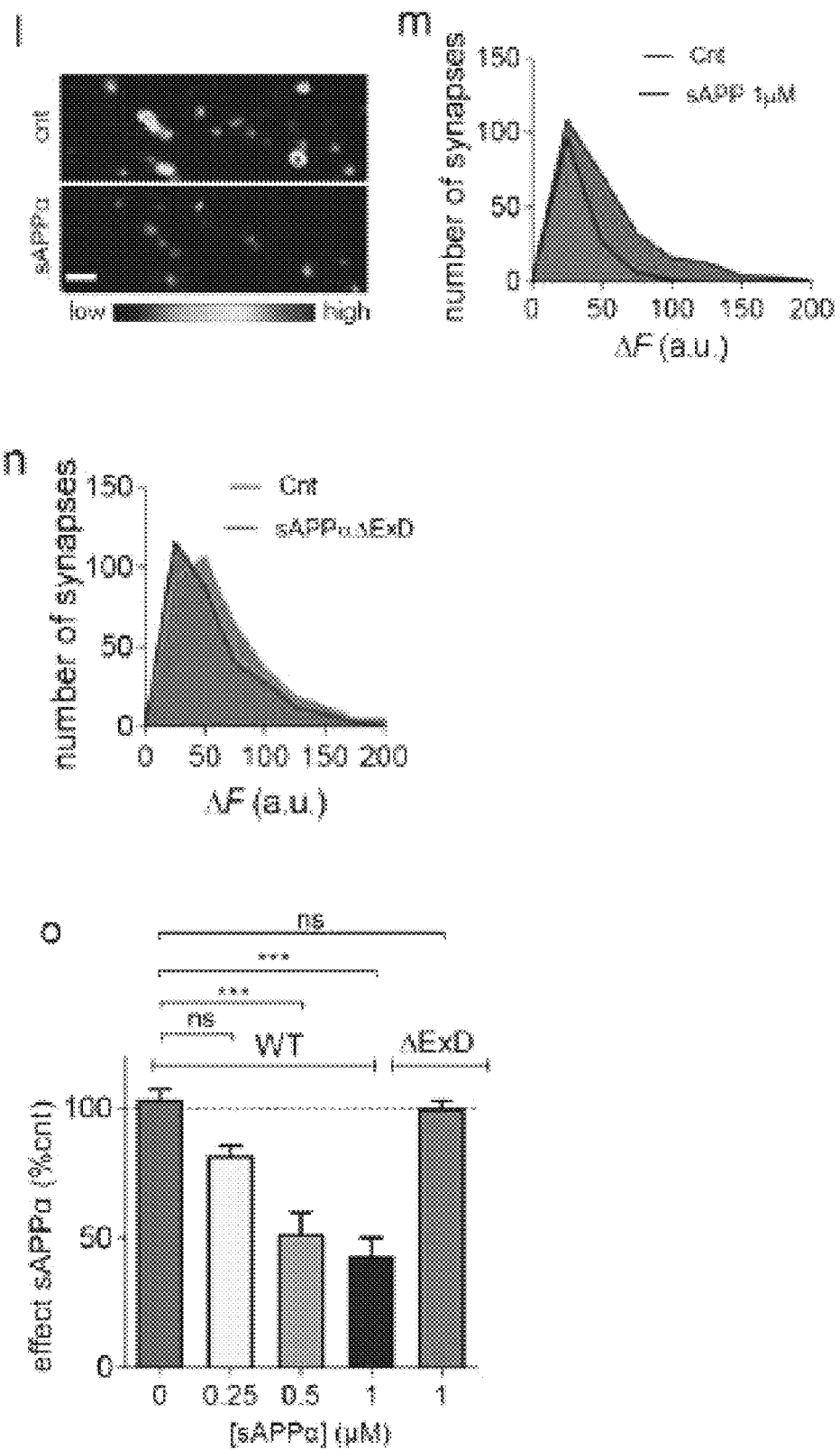
Figure 8:
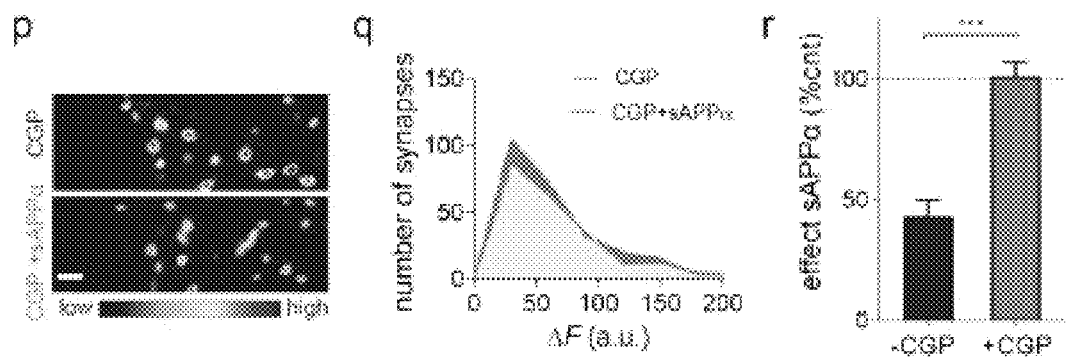
Figure 9:
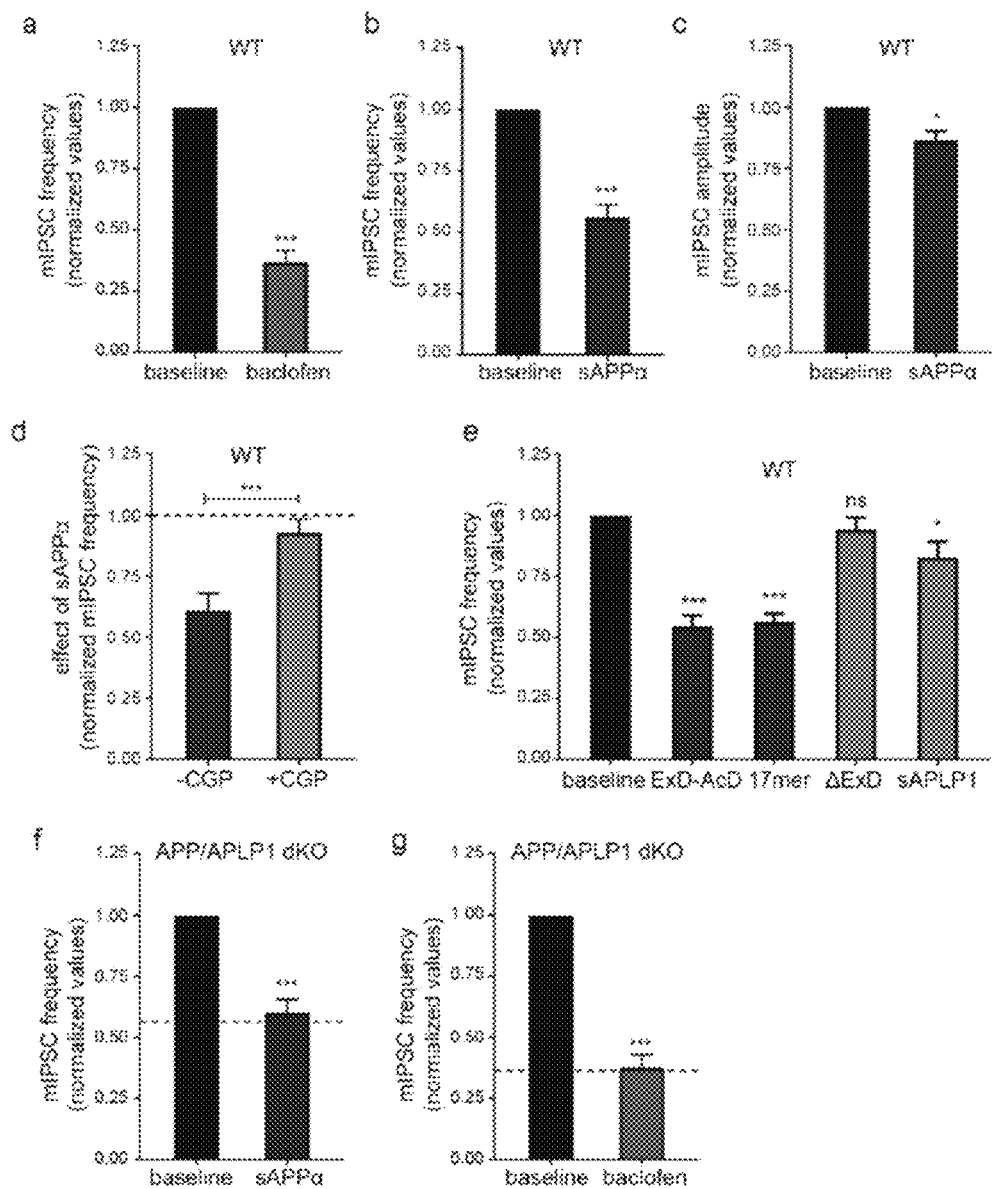
FIG. 9. sAPPα reduces mIPSC frequency via GABA$_B$Rs in cultured hippocampal neurons. a, Average mIPSC frequency normalized to baseline recorded from wild type neurons before (baseline) and after treatment with baclofen, a GABA$_B$R agonist. (n=12, paired t-test) b,c, Average mIPSC frequency (b) and amplitude (c) normalized to baseline recorded from wild type neurons before (baseline) and after treatment with sAPPa. (n=13, paired t-test). d, Quantification of the effect of sAPPa on m IPSC frequency normalized to baseline either without (blue) or with (green) preincubation with CGP55845 (CGP), a GABA$_B$R antagonist. Dotted line denotes baseline. (n=14-17, unpaired t-test). e, Average mIPSC frequency normalized to baseline recorded from wildtype neurons before (baseline) and after treatment with either sAPPa ExD-AcD, 17mer (APP695 204-220AA), sAPPαΔExD, or sAPLP1. (n=17-20, one way ANOVA with Dunnett's post hoc analysis). f,g, Average mIPSC frequency normalized to baseline recorded from App/Aplp1 dKO primary hippocampal neurons before (baseline) and after treatment with either sAPPα (j) or baclofen (k). Dotted line denotes effect in wildtype neurons. (n=14, paired t-test). (Error bars represent s.e.m. The number of neurons is defined as n from 2 (a,g) or 3 (b,c,d,e,f) independent experiments. *P<0.05; ***P<0.001).

Measuring Miniature Excitatory and Inhibitor, Postsynaptic Currents in Hippocampal Cultures (mEPSCs & mIPSCs)

mEPSCs & mIPSCs are measured in cultured primary hippocampal neurons at baseline and following acute application of agonists. Excitatory terminals selectively express the sushi domain-containing $GABA_BR1a$ isoform (ref18), where it functions to inhibit neurotransmitter release (ref 24). Acute exposure of primary hippocampal neurons from wild type mice to 30µM baclofen, a $GABA_BR$ agonist, or 250 nM sAPPα (Fc cleaved) reduces the frequency of miniature excitatory postsynaptic currents (mEPSCs) by 68% (FIG. 8 a,b) and 39% (FIG. 8 c,d), respectively, with no effect on mEPSC amplitude (FIG. 8e). Pretreatment with the $GABA_BR$ antagonist CGP55845 (CGP, 5 µM) blocks the effect of sAPPα on mEPSC frequency (FIG. 8 f,g). Acute application of the 17mer peptide or APP695 ExD-AcD fragment, but not sAPPαΔExD or sAPLP1, reduces mEPSC frequency to a similar degree as sAPPα (FIG. 8 h,i). sAPPα binding to $GABA_BRs$ located at GABAergic synapses should also modulate inhibitory synaptic transmission. Acute application of 30 µM baclofen or 250 nM purified sAPPα reduces the frequency of miniature inhibitory postsynaptic currents (mIPSCs) by 63% (FIG. 8a, 9a) and 44% (FIG. 8c, 9b), respectively, which is blocked by pretreatment with the $GABA_BR$ antagonist CGP55845 (CGP, 5 µM) (FIG. 8f, 9d). Application of sAPPα causes a minor (14%) reduction on mIPSC amplitude (FIG. 8e, 9c). Again, the APP695 ExD-AcD fragment or the 17mer peptide, but not sAPPαΔExD, reduce mIPSC frequency to a similar extent as sAPPα (FIG. 8i, 9e). Finally, sAPLP1, which does not bind $GABA_BR1a$, causes a minor (17%) reduction in mIPSC frequency (FIG. 8h, 9e). Taken together, these data show that sAPPα reduces both glutamatergic and GABAergic quantal synaptic transmission through a $GABA_BR1a$ isoform-dependent mechanism. Baclofen is known to reduce the frequencies of mEPSCs and mIPSCs, which we have also confirmed. Agonists show a similar effect in reducing mEPSC and mIPSC frequency, which we have confirmed for a 107aa binding region of APP. To confirm that the agonist is acting through $GABA_BR1a$, the agonist is tested in cultures with shRNA mediated knockdown of $GABA_BR1a$ or antisense oligonucleotides mediated exon skipping of the exon encoding the Sushi domain 1 of $GABA_BR1a$. Antagonists are tested by treatment in combination with the agonist, Baclofen. A peptide with the extension domain sequence (NVDSADAEEDDSDVWWGGADTDYADGSEDKVVE) reduces the frequencies of mEPSCs and mIPSCs and therefore acts as an agonist. As an antagonist we test an antibody against the sushi domain sequence (SEQ ID No: 5): TSEGCQIIHPPWEGGIRYRGLTRDQVKAIN-FLPVDYEIEYVCRGEREVVGPKVRKCLANG SWTDMDTPSRCV. An antibody specifically binding to this domain which acts as an antagonist increases the frequencies of mEPSCs and mIPSCs. sAPPα also reduces mEPSC and mIPSC frequency in App/Aplp1 dKO cultures (FIG. 8j, 9f), excluding the possibility that sAPPα interferes with a complex of full-length APP and $GABA_BR1$ to exert its effect on $GABA_BR$ signaling. Furthermore, baclofen has similar effects on mEPSC and mIPSC frequency in App/Aplp1 dKO cultures (FIG. 8k, 9g) as in wild type cultures (FIG. 8b, 9a), indicating that full-length APP is not needed for normal $GABA_BR$ function under basal conditions.

Example 5

$GABA_BR1a$ Mediates Presynaptic Inhibition Induced by sAPPα.

The decrease in mEPSC frequency but not amplitude following sAPPα treatment suggests a decrease in release probability. We assessed the effect of sAPPα on synaptic vesicle recycling (ref6) using the activity-dependent dye FM1-43. We measured density (D) and intensity (ΔF) of FM1-43 uptake in presynaptic vesicles turned over by stimulation of 30 action potentials (APs) at a rate of 1 Hz in cultured hippocampal neurons. The total presynaptic strength (S=ΔF×D) 15 min after addition of sAPPα substantially decreases across synaptic populations (FIG. 8l, m) in a dose dependent manner (FIG. 8o), reaching 57% reduction at 1 µM sAPPα (FIG. 8m,o). Deletion of the ExD (sAPPαΔExD, 1 µM) completely abolishes the ability of sAPPα to inhibit presynaptic vesicle recycling (FIG. 8n,o), and the effect of sAPPα on presynaptic strength is occluded by the $GABA_BR$ antagonist CGP54626 (CGP, FIG. 8p-r), indicating that $GABA_BR1a$ mediates the presynaptic inhibition induced by sAPPα.

Example 6

Measuring Long-Term Potentiation in Hippocampal Slices

Long-term potentiation (LTP) is induced by stimulation of Schaffer collateral fibers and the response of CA1 pyramidal neurons is measured by extracellular recordings. For measuring antagonists, a primed burst stimulation protocol is used to activate $GABA_BR$ receptors. Under this protocol, an antagonist blocks induction of LTP. For measuring agonists, a non-primed high frequency stimulation protocol is used. Under this protocol, an agonist facilitates LTP.

Figure 10:
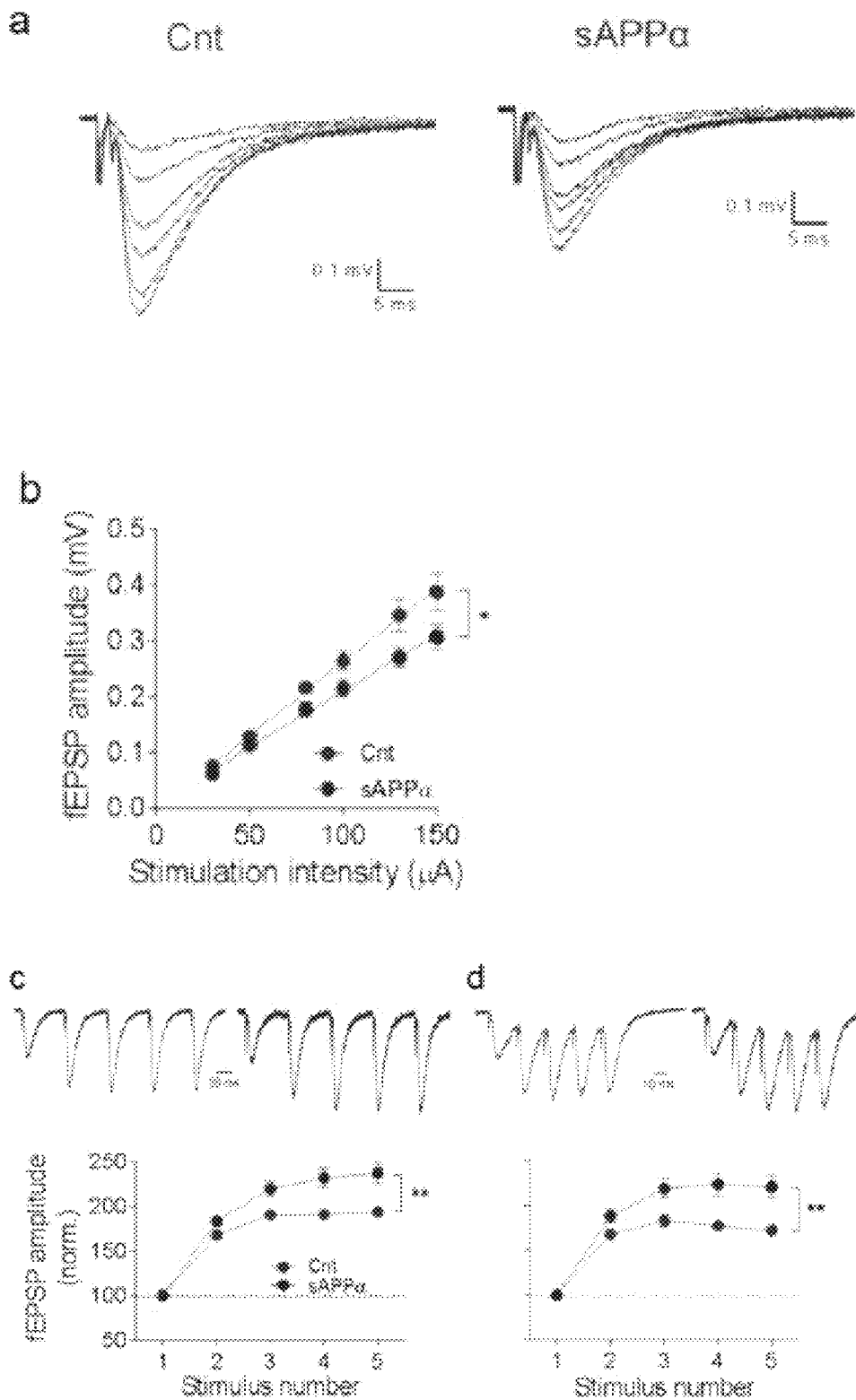
FIG. 10. sAPPα reduces basal synaptic transmission and increases short-term plasticity via GABA$_B$R at Schaffer collaterals. a,b, Representative traces of fEPSPs (a) and input-output curves (b) recorded at SCs from hippocampal slices incubated without (grey) or with sAPPα (blue). (Cnt, n=9, N=7; sAPPα, n=12, N=7). c-e, Representative traces (upper) and average fEPSP amplitude (lower) in response to high-frequency burst stimulation at 20 Hz (c), 50 Hz (d), and 100 Hz (e) (for each frequency: n=10, N=7 for Cnt; n=12, N=7 for sAPPα) in slices incubated without (grey) or with sAPPα (blue). fEPSPs were normalized to the peak amplitude of the first response. f,g, Representative traces of fEPSPs (f) and input-output curves (g) recorded from hippocampal slices incubated with CGP 54626 (CGP) alone (grey) and slices incubated with CGP+sAPPα (green). (CGP, n=9, N=4; CGP+sAPPα, n=8, N=4). h-j, Representative traces (upper) and average fEPSP amplitude (lower) in response to high-frequency burst stimulation at 20 Hz (h), 50 Hz (i), and 100 Hz (j)(for each frequency: n=9, N=4 for CGP; n=8, N=4 for CGP+sAPPα) from slices incubated with CGP alone (grey) or with CGP+sAPPα (green). fEPSPs were normalized to the peak amplitude of the first response. (Error bars shown represent s.e.m. The number of slices is defined by n, the number of mice by N. Two-way ANOVA analysis; *P<0.05: P<0.01; *P<0.001).
Figure 10:
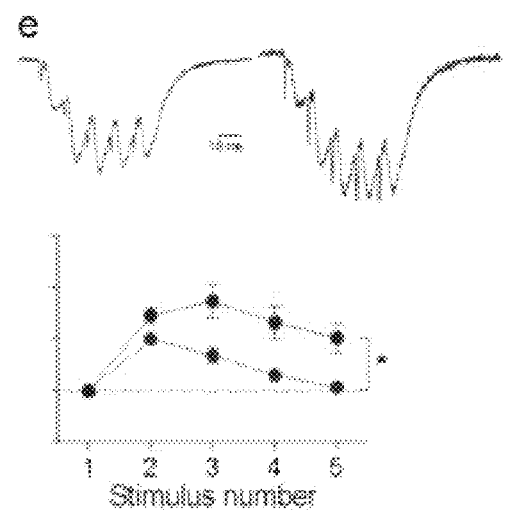
Figure 10:
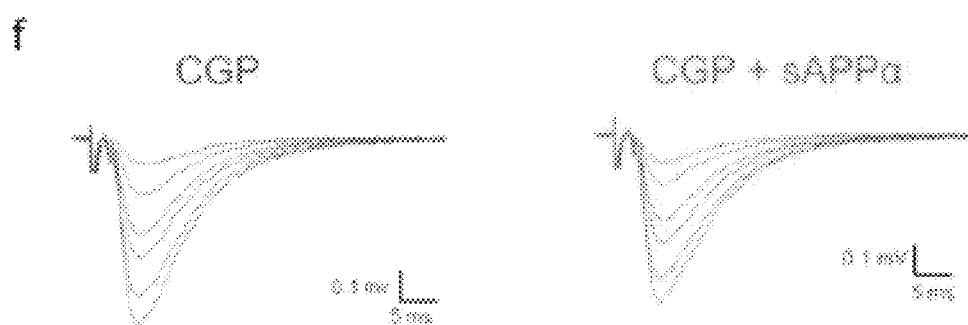
Figure 10:
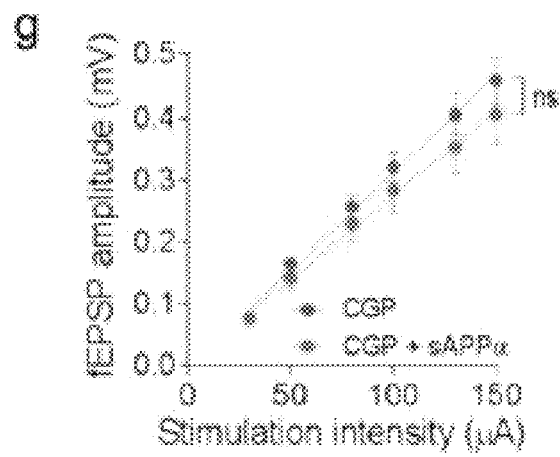
Figure 10:
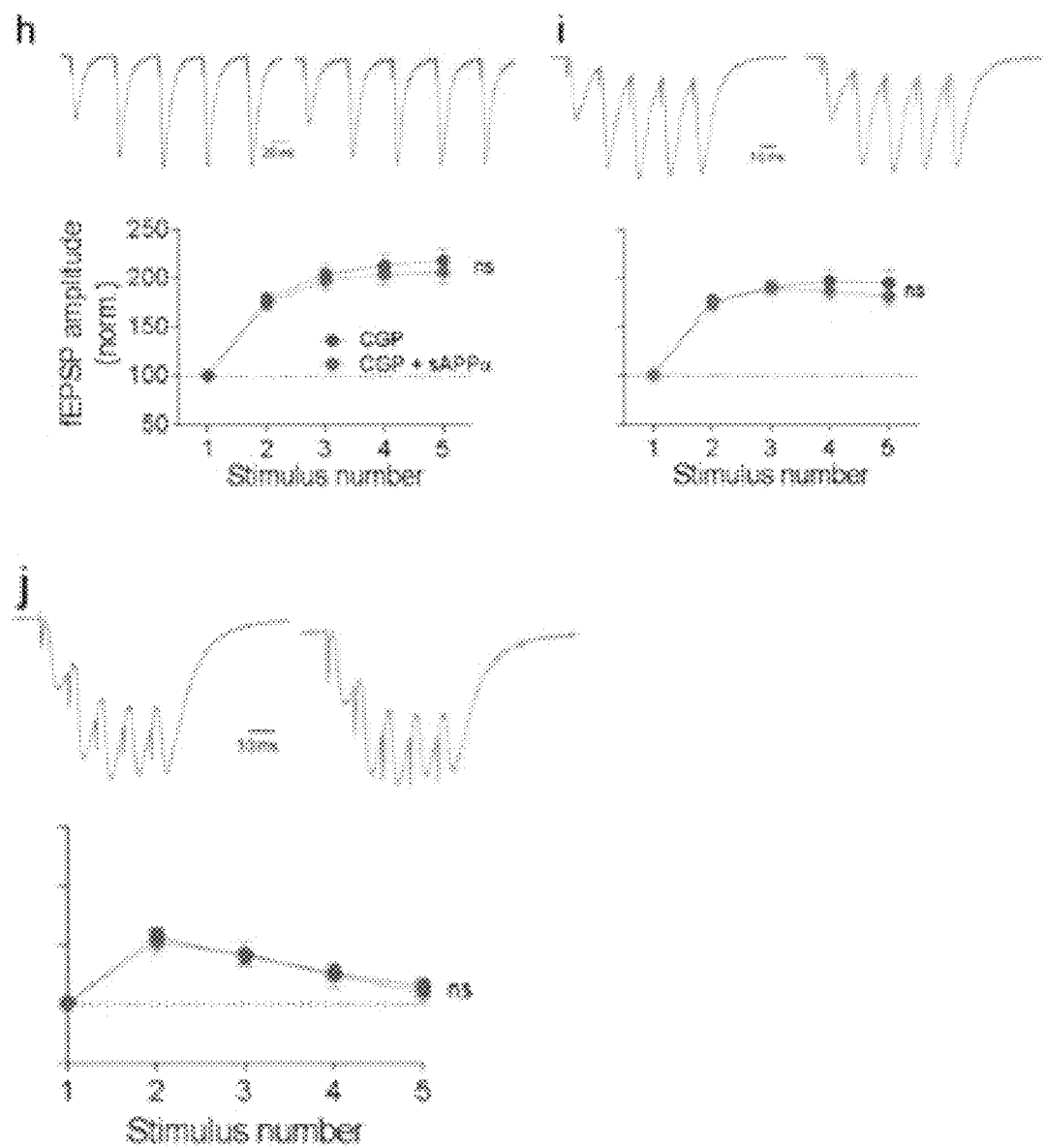

We assessed the effect of sAPPα on the synaptic properties of Schaffer collateral (SC) synapses in mouse hippocampus. Field EPSPs (fEPSPs) in the stratum radiatum of the CA1 area are elicited using a gradient of stimulation intensities (30-150 µA) after 2 h incubation with or without 1 µM sAPPα (FIG. 10a). sAPPα affects basal synaptic transmission evoked by low frequency stimulation of 0.1 Hz at the SC synapses, reducing fEPSP amplitude and causing a 23% decrease in the slope of the input/output curve (FIG. 10b). As change in probability of neurotransmitter release inversely correlates with a change in short-term facilitation, we applied a burst of 5 stimuli at 3 different frequencies (20, 50, and 100 Hz) to induce short-term facilitation at the SC. Facilitation was significantly higher for each frequency tested in sAPPα-incubated compared to control slices (FIG. 10c-e). Preincubation with the $GABA_BR$ antagonist CGP54626 (CGP, 10 µM) for 20 min before the incubation with sAPPα blocked its effects on the peak amplitude of the fESPS and the input/output slopes (FIG. 10f-g). Accordingly, CGP occluded sAPPα-induced augmentation of short-term facilitation at 20, 50, and 100 Hz burst frequencies (FIG. 10h-j). Altogether, these results suggest that sAPPα inhibits glutamate release by acting on presynaptic GABA$_B$Rs at the SC synapses.

As a confirmation that these effects are mediated through GABA$_B$R1a shRNA mediated knockdown of GABA$_B$R1a is employed. Alternatively, antisense oligonucleotides mediated exon skipping of the exon encoding the Sushi 1 domain of GABA$_B$R1a is considered.

A peptide with the extension domain sequence (NVDSA-DAEEDDSDVWWGGADTDYADGSEDKVVE) facilitates LTP and therefore acts as an agonist. As an antagonist we test an antibody against the sushi domain 1 sequence TSEGCQIIHPPWEGGIRYRGLTRDQVKAIN-FLPVDYEIEYVCRGEREVVGPKVRKC LANGSWTD-MDTPSRCV. An antibody specifically binding to this domain which acts as an antagonist blocks induction of LTP.

Example 7

Generation of Nanobodies Specifically Binding to the Sushi Domain 1 of the GABA$_B$1a Receptor Nanobodies are generated as described before (Vincke, C. & Muyldermans, S. Introduction to heavy chain antibodies and derived nanobodies. *Methods Mol Biol* 911, 15-26 (2012)). In brief, an alpaca and a dromedary are injected subcutaneously on days 0, 7, 14, 21, 28, 35 with about 250 µg of human sushi domain 1 of the GABA$_B$1a receptor (sequence is SEQ ID No: 5: TSEGCQIIHPPWEGGIRYR-GLTRDQV KAINFLPVDYEIEYVCRGEREVVGPK-VRKCLANGSWTDMDTPSRCV) per injection. After these six rounds of immunization, antibodies of different IgG subclasses are obtained by successive affinity chromatography on protein A and protein G columns. Total plasma and three purified IgG subclasses (IgG1, IgG2 and IgG3) from both alpaca and dromedary are tested by ELISA to assess the immune response to sushi domain 1 of the GABA$_B$1a receptor. In the dromedary, there is immune response in all IgG subclasses with best response in IgG1. The immune response raised in alpaca is very low. Two VHH libraries (one from the alpaca and one from the dromedary immunized with sushi domain 1 of the GABA$_B$1a receptor) are constructed using conventional methods (Hoogenboom, H. R., et al. Antibody phage display technology and its applications. *Immunotechnology* 4, 1-20 (1998); Winter, G., Griffiths, A. D., Hawkins, R. E. & Hoogenboom, H.R. Making antibodies by phage display technology. *Annu Rev Immunol* 12, 433-455 (1994)) and screened for the presence of sushi domain 1 of the GABA$_B$1a receptor-specific nanobodies. To this end, total RNA from peripheral blood lymphocytes is used as template for first strand cDNA synthesis with oligo(dT) primer. Using this cDNA, the VHH encoding sequences 30 are amplified by PCR, digested with PstI and NotI, and cloned into the PstI and NotI sites of the phagemid vector pHEN4. From the alpaca, a VHH library with a high number of independent transformants is obtained. About 70% of these transformants harboured the vector with the right insert size. In a similar way, from the dromedary, a VHH library with many independent transformants is obtained. About 80% of the transformants from the dromedary library harboured the vector with the right insert size.

Each library is subject to four consecutive rounds of panning, performed on solid-phase coated antigen (concentration: 100 µg/ml, 10 µg/well). The enrichment for antigen-specific phages after each round of panning is assessed by comparing the number of phages eluted from antigen-coated wells with the number of phages eluted from only-blocked wells. The enrichment is also evaluated by polyclonal phage ELISA. Based on these assays, the library obtained from alpaca is enriched for antigen-specific phages only after $4^{th}$ round of panning. In contrast, the library from dromedary is enriched for antigen-specific phages after $2^{nd}$, $3^{rd}$ and $4^{th}$ rounds, with best enrichment factors after $2^{nd}$ and $3^{rd}$ rounds.

From the alpaca library, about 180 individual colonies identified after the $4^{th}$ round of panning are randomly selected and analyzed by ELISA for the presence of sushi domain 1 of the GABA$_B$1a receptor-specific nanobodies in their periplasmic extracts. Out of 180 colonies, 80% scored positive in this assay. Sequencing of 50 of these positive colonies identified a number of different nanobodies. All these nanobodies belong to the same family.

From dromedary library, 140 individual colonies (47 from the $2^{nd}$ and 95 from the $4^{th}$ round of panning) are randomly selected and analyzed by ELISA for their specificity for sushi domain 1 of the GABA$_B$1a receptor. Out of these 140 colonies, 50% of the colonies (70% thereof from $2^{nd}$ round and 30% thereof from $4^{th}$ round) score positive in this assay. Sequencing of 30 positive colonies identified a number of different nanobodies representing 3 different families. These mutations are likely derived from PCR errors during construction of libraries. From these two libraries, one nanobody (Nb1) is selected from alpaca library, and three nanobodies (Nb2, Nb3, Nb4) are selected from dromedary library, each representing an individual family.

The 4 constructs are expressed in *E. coli* by subcloning into BamHI/XhoI sites of or pET30a (Novagen), to obtain His$_6$-tagged peptides. These are purified using conventional Ni-affinity purification protocol (Qiagen). Briefly, proteins are overexpressed in C41 (DE3) cells overnight at 25° C. in TB medium after induction with 1 mM IPTG. Cells are lysed by high-pressure cell cracker in lysis buffer (TBS containing 15 mM imidazole), and supernatant is cleared by centrifugation at 12,000 rpm for 20 minutes. Supernatant is incubated with Ni-agarose for 30 minutes, followed by washes with 200 volumes of lysis buffer, and eluted in TBS containing 250 mM imidazole. In a second step, nanobodies are purified by size-exclusion chromatography on Superdex S-75 columns in TBS buffer and concentrated using Centricon units (Millipore).

Isothermal Titration Calorimetrics

The heat of binding of selected nanobodies to sushi domain 1 of the GABA$_B$1a receptor is measured using the Omega isothermal titration calorimeter (Microcal). Samples containing sushi domain 1 of the GABA$_B$1a receptor in TBS are titrated with selected nanobodies in TBS at in 0 isothermal chamber kept at the constant temperature of 25° C. Samples are filtered through 0.2 mM syringe and degassed before measurements. Aliquots (10 µL) of nanobodies are added consequently each 10 minutes (28 aliquotes in total) to allow for the chamber to equilibrate. The resulting change in the heat required to equilibrate the chamber to the constant temperature is recorded and processed using the single-site binding equation (Wiseman, T., Williston, S., Brandts, J. F. & Lin, L. N. Rapid measurement of binding constants and heats of binding using a new titration calorimeter. *Analytical biochemistry* 179, 131-137 (1989)) in the Origin 7.0 software (Microcal).

Transmission Electron Microscopy

The proteins for TEM studies are expressed in *E. coli* and purified as described above. Samples containing either sushi domain 1 of the GABA$_B$1a receptor (0.2 mM) alone or sushi domain 1 of the GABA$_B$1a receptor with equimolar concentrations of selected nanobodies are imaged after incubation for 4 weeks with shaking in 50 mM Tris-HCl (pH 8) at 25° C. Aliquots (5 sL) of the incubated protein preparations are adsorbed to carbon-coated FormVar film on 400-mesh copper grids (Plano GmbH, Germany) for 1 min. The grids are blotted, washed twice in 50 µL droplets of Milli-Q water, and stained with 1% (wt/vol) uranylacetate (Sigma). Samples are studied with a JEOL JEM-2100 microscope at 200 kV. Images are processed using iTEM software.

Materials and Methods:

Animals

All animal experiments were conducted according to the KU Leuven and Tel Aviv University ethical guidelines and approved by the KU Leuven or the Tel Aviv University Committee on Animal Care.

Plasmids

APP-Fc constructs were generated by PCR-amplifying the following regions of mouse APP695: sAPPα=18-612aa; sAPP-=18-596aa; GFLD=18-128aa; CuBD=129-194aa; AcD-ExD=195-298aa; ExD=195-227aa; AcD=228-298aa; E2=299-494aa; sAPPαAExD=19-194aa & 228-596aa. APLP-Fc constructs were generated by PCR-amplifying the ectodomain without the signal sequence of mouse APLP1 (38-583aa) and mouse APLP2 (32-636aa). Each of the PCR fragments were subcloned between and in frame with the prolactin signal peptide and human Fc in the pCMV6-XL4 vector using Gibson Assembly (NEB). The cDNA clone for human $GABA_BR2$ was obtained from the cDNA Resource Center and the cDNA clone for human $GABA_BR1b$ human was obtained from origene. The N-terminal domain lacking the signal sequence was synthesized for $GABA_BR1a$ or generated by PCR-amplification for $GABA_BR1b$ and $GABA_BR2$. The fragments were subcloned into pDisplay (Invitrogen), making a fusion protein with the transmembrane domain of the platelet derived growth factor receptor and an N-terminal HA epitope tag.

Biochemical Fractionation

Seven P21 rat brains were homogenized in homogenization buffer (0.32 M Sucrose, 1 mM NaHC03, 1 mM MgCl2, 0.5 mM Cacl2) with protease inhibitor using a glass Dounce homogenizer. "Homogenates" were centrifuged at 1000×g for 15 minutes at 4° C. Postnuclear supernatants were centrifuged at 10,000×g for 20 minutes. The pellet P2 containing "crude membranes" was resuspended in Solution B (0.32 M sucrose, 1 mM NaHC03, with protease inhibitors) and loaded onto sucrose gradient (1.2M, 1M, 0.5M sucrose) and centrifuged at 32,500×g for 2 hrs. Pure "synaptosome" was collected from between the 1.2M and 1M sucrose interphase. Synaptosomes were diluted in Buffer B and 0.5% Triton X-100, incubated for 30 minutes at 4° C. to enrich for presynaptic proteins34, and centrifuged at 32,500×g for 25 mins to yield a supernantent with "triton soluble" synaptosomes. Pellet was resuspended in Buffer B and loaded on a second sucrose gradient (2M, 1.5M, 1M sucrose) and centrifuged at 200,000 g for 2 hrs. Triton insoluble fraction was collected from between the 1.5M and 2M sucrose interface and centrifuged at 200,000 g for 20 mins. The pellet was then resuspended as the final "triton insoluble" fraction. Protein content was quantified in each fraction by Pierce BCA protein assay (Thermo Fisher) and equal protein amounts were loaded onto SDS-PAGE and immunoblotted using the following primary antibodies: rabbit anti-APP (c-terminal, B63,35), rabbit anti-APLP1 (W1CT, gift of Dominic Walsh36); rabbit anti-APLP2 (W2CT, gift of Dominic Walsh36), guinea pig anti-vGLUT1 (Millipore), mouse anti-synaptophysin (Sigma), mouse anti-PSD-95 (Thermo Scientific), and mouse anti-NR2A (BD Biosciences).

Immunohistochemistry

P35 C57/B16 wild type were transcardially perfused with 4% paraformaldehyde. Brains were dissected, post fixed with 4% paraformaldehyde for 1 hour, cryopreserved in 30% sucrose solution, and embedded in Tissue-Tek@ OCT for freezing. Coronal cryosections were prepared with 16 µm thickness. Sections were permeabilized and blocked at RT for 2 hour in PBS, 0.5% Triton X-100, 10% normal horse serum, and incubated with the primary antibody at 4° C. O/N followed by 2 hr incubation with Fluorophore-conjugated secondary antibodies (Jackson ImmunoResearch or Invitrogen). The following primary antibodies were used: rabbit anit-APP (c-terminal, B63,35), guinea pig anti-vGLUT1 (Millipore), mouse anti-PSD-95(Thermo Scientific), guinea pig anti-VGAT (Synaptic Systems), mouse anti-Gephyrin (Synaptic Systems). Fluorophore-conjugated secondary antibodies were from Jackson ImmunoResearch or Invitrogen. Images were acquired by super-resolution structured illumination microscopy on a Zeis Elyra S.1.

Protein Purifications

Secreted Fc-tagged proteins were expressed by stable or transient transfection (using PEI transfection vector) in HEK293 cells and collected in serum-free Opti-MEM (Thermo Fisher Scientific, Inc.). For Fc-tagged proteins used in the proteomics screen and cell-surface binding assays, conditioned medium was run on an affinity column packed with Protein-G Plus Agarose fast flow resin (Pierce) using a gravity-flow system. Affinity column was washed with 250 ml wash buffer (50 mM HEPES pH 7.4, 300 mM NaCl) and eluted with 10 ml IgG elution buffer (Pierce). For non-Fc proteins used in functional and in vitro binding assays, following passage of conditioned medium through the column packed with Protein-G Agarose, the column was washed with 250 mL wash buffer (50 mM Tris pH 8.0, 450 mM NaCl, 1 mM EDTA), the Fc tag was cleaved by O/N incubation with GST-tagged 3C PreScission Protease (GE Healthcare) in cleavage buffer (50 mM Tris pH 8.0, 150 mM NaCl, 1 mM EDTA, 1 mM DTT), and the cleaved protein was collected in the eluate. The protease was subsequently separated from the eluted proteins using a Glutathione Sepharose (GE Healthcare) packed column. Proteins were concentrated using Amicon Ultra 10 kDa MWCO centrifugal filter units (Millipore), dialyzed against PBS, and protein concentration determined by Bradford assay (Bio-Rad).

Affinity Chromatography for Mass Spectrometric Identification of sAPP-Binding Proteins Affinity chromatography for mass spectrometric identification of binding partners was performed as described previously 37,38. For each Fc bait, three rat brains were homogenized in homogenization buffer (4 mM HEPES, 0.32 M sucrose) with protease inhibitors using a glass Dounce homogenizer. Homogenates were centrifuged at 1000×g for 25 mins at 4° C. Supernatants were centrifuged for at 14,000×g for 25 mins. The pellet P2 containing crude synaptosomes was resuspended in homogenization buffer and centrifuged at 10.000 g for 20 minutes, yielding pellet P2' containing washed crude synaptosomes. Pellet P2 was extracted in 20 mM Tris pH 8.0, 0.1 mM $CaCl_2$) and 1% Triton X-100 for 2.5 hours at 4° C. The extracts were centrifuged at 100,000×g for 1 hour, and the final supernatants collected for affinity chromatography. Protein-G Plus Agarose fast flow resin (Pierce) (Pierce, 500 µl slurry) pre-coupled to 100 µg human Fc control protein, sAPPα-Fc or sAPPβ-Fc was added to synaptosome extracts and rotated O/N at 4° C. The agarose resin with bound proteins were then packed into Poly-Prep chromatography columns (Bio-Rad) and washed with 50 ml of high-salt wash buffer (50 mM Hepes pH 7.4, 300 mM NaCl, 1 mM EDTA) with protease inhibitors, followed by a wash with 10 ml low salt wash buffer (50 mM Hepes pH 7.4, 150 mM NaCl, 1 mM EDTA) with protease inhibitors). Bound proteins were eluted from the beads by incubation with Pierce elution buffer and TCA precipitated O/N. For the MS analysis only proteins with more than two spectra counts from a single pull-down were included, and any proteins that had one or more spectra counts in the Fc controls were excluded. Finally, the dataset was filtered to only include transmembrane, cell-surface proteins using Panther and Uniprot databases.

MudPIT (LCLC-MS/MS) LTO XL Mass Spectrometry Analysis

Protein precipitates were solubilized in 8M urea (8 M) and processed with ProteasMAX (Promega) per the manufacturer's instruction. The samples were subsequently reduced by TCEP (tris(2carboxyethyl)phosphine, 5 mM, room temperature, 20 min), alkylated in the dark by 10 mM iodoacetamide (10 mM, 20 min), digested with Sequencing Grade Modified Trypsin (Promega) overnight at 37° C., and the reaction was stopped by acidification to 5% final with formic acid. The entire protein digest was pressure-loaded into a 250-µm i.d capillary packed with 2.5 cm of 10 µm Jupiter C18 resin (Phenomenex) followed by an additional 2.5 cm of 5-µm Partisphere strong cation exchanger (Whatman)39,40. The column was washed with buffer containing 95% water, 5% acetonitrile, and 0.1% formic acid. After washing, a 100-µm i.d capillary with a 5-µm pulled tip packed with 15 cm of 4-µm Jupiter C18 resin (Phenomenex) was attached to the filter union and the entire split-column (desalting column-union-analytical column) was placed in line with an Agilent 1200 quaternary HPLC and analyzed using a modified 6-step separation described previously41. The buffer solutions used were 5% acetonitrile/0.1% formic acid (buffer A), 80% acetonitrile/0.1% formic acid (buffer B), and 500 mM ammonium acetate/5% acetonitrile/0.1% formic acid (buffer C). MS analysis was performed on a LTQ XL mass spectrometer using a standard data dependent acquisition strategy with the following settings. MS1 scan range was from 300-2000 M/Z. We used CID fragmentation with a minimal signal required for selection for MS/MS of 1000, an isolation width 2.0, and Normalized collision energy of 35.0. The default charge state setting was set to 2, we rejected charge 1 ions and activation (Q) of 0.25 with an activation time of 30.0. the top 5 most intense peaks were considered for MS/MS.

Analysis of Tandem Mass Spectra

Protein identification and quantification and analysis were done with Integrated Proteomics Pipeline—IP2 (Integrated Proteomics Applications, Inc., San Diego, Calif. (http://www.integratedproteomics.com/) using ProLuCID, DTASelect2, Census, and QuantCompare. Spectrum raw files were extracted into ms1 and ms2 files using RawExtract 1.9.9 (http://fields.scripps.edu/downloads.php), and the tandem mass spectra were searched against Uniprot mouse protein databases (downloaded on Apr. 1, 2013). In order to accurately estimate peptide probabilities and false discovery rates, we used a target/decoy database containing the reversed sequences of all the proteins appended to the target database42. Tandem mass spectra were matched to sequences using the ProLuCID (modified Sequest) algorithm with 3000 ppm peptide mass tolerance for precursor ions and 600 ppm for fragment ions. ProLuCID searches were done on an Intel Xeon cluster running under the Linux operating system. The search space included all fully- and half-tryptic peptide candidates that fell within the mass tolerance window with no miscleavage constraint. Carbamidomethylation (+57.02146 Da) of cysteine was considered as a static modification. The validity of peptide/spectrum matches (PSMs) was assessed in DTASelect43,44, using two SEQUEST45 defined parameters, the crosscorrelation score (XCorr), and normalized difference in cross-correlation scores (DeltaCN). The search results were grouped by charge state (+1, +2, +3, and greater than +3) and tryptic status (fully tryptic, half-tryptic, and nontryptic), resulting in 12 distinct sub-groups. In each one of these sub-groups, the distribution of Xcorr, DeltaCN, and DeltaMass values for (a) direct and (b) decoy database PSMs was obtained, then the direct and decoy subsets were separated by discriminant analysis. Full separation of the direct and decoy PSM subsets is not generally possible; therefore, peptide match probabilities were calculated based on a nonparametric fit of the direct and decoy score distributions. A peptide confidence of 0.95 was set as the minimum threshold. The false discovery rate was calculated as the percentage of reverse decoy PSMs among all the PSMs that passed the confidence threshold. Each protein identified was required to have a minimum of two peptides and have at least one tryptic terminus. After this last filtering step, we estimate that both the protein false discovery rates were below 1% for each sample analysis.

Cell Surface Binding Assay

HEK293T cells were transfected with GFP (as negative control) or pdisplay-GABABR-1a, -1b, or -2 plasmids using Fugene6 (Promega). Twenty-four hours after transfection, the cells were incubated with Fc (as negative control) or the various Fc-tagged APP proteins (500 nM, in Dulbecco's modified Eagle's medium [DMEM] supplemented with 20 mM HEPES [pH 7.4]) for 1 hr at RT. After three brief washes with DMEM/20 mM HEPES (pH 7.4), cells were fixed in 4% paraformaldehyde, 4% sucrose in PBS. Cells were blocked in 3% BSA in PBS, and staining was performed in detergent-free conditions without cell permeabilization. Primary antibody mouse anti-HA (Covance) was used to detect HA-tagged GABABR transfected cells. Cy3-conjugated donkey anti-human IgG (Jackson ImmunoResearch) was used to detect bound Fc proteins. Fluorophore-conjugated secondary antibodies were from Jackson ImmunoResearch or Invitrogen. Images were captured on a Leica SP5 confocal microscope (Leica Microsystems, Bannockburn, Ill.). Image thresholding was set with ImageJ software using constant settings per experiment and the area of Fc binding was measured relative to cell area.

Isothermal titration calorimetry (ITC)

All ITC experiments were carried out on a MicroCal iTC200 system. For ITC experiments involving APP constructs expressed in HEK293 cells, the purified GABABR1a-Sushi1 domain, sAPPα, CuBDAcD, AcD and CuBD constructs were buffer-exchanged by size exclusion chromatography in 20 mM Na-HEPES pH 7.0, 150 mM NaCl supplemented with 5 mM CaCl2. Concentrated samples were diluted and degassed before the experiment at the concentrations reported in the FIG. legends. sAPP fragments (all of them at 30 µM) were placed in the MicroCal sample cell and matching buffer was placed in the reference cell. Sushi1 (300 µM) was in the syringe and was injected into the cell in a series of 1 µL injections at 25° C. All the datasets were subtracted with a reference data consisting of serial injections of Sushi1 in the cell, containing buffer only under the same conditions. For ITC experiments involving synthetic APP peptides, the Sushi-1 protein was dialysed overnight to PBS buffer. The 17-mer peptide was resuspended in H2O:acetonitrile (5:1) at a stock concentration of 3 mM, and diluted in PBS to 300 uM. In order to avoid buffer-buffer mismatches, the same amount of H2O:acetonitrile mixture was also added when diluting the protein to a 30 uM concentration. The 9-mer peptide was resuspended in PBS. Titrations comprised 26×1.5 sL injections of peptide into the protein, with 90 s intervals. An initial injection of ligand (0.5 sL) was made and discarded during data analysis. The raw ITC data were fitted to a single binding site model using the Microcal LLC ITC200 Origin software provided by the manufacturer.

Primary Neurons

Hippocampal neurons were cultured from E18 C57/B16 wild type mice or APP/APLP1 dKO mice (provided by Ulrike Muller46) and plated on poly-D-lysine (Millipore), and laminin (Invitrogen) coated coverslips (Nalge Nunc International). Neurons were maintained in Neurobasal medium (Invitrogen) supplemented with B27, glucose, glutamax, penicillin/streptomycin (Invitrogen) and 25 µM β-mercaptoethanol.

Electrophysiological Recordings of Cultured Neurons

Single neurons from wild type or APP/APLP1 null mutant embryos (E18) were recorded within the large neuronal network at DIV 12-15. The intracellular whole-cell pipette medium contained (in mM): 136 KCl, 18 HEPES, 4 Na-ATP, 4.6 MgCl2, 15 Creatine Phosphate, 1 EGTA and 50 U/ml Phospocreatine Kinase (300 mOsm, pH 7.30). Regular external solution contained 2 mM/2 mM Ca2+/Mg2+(in mM: 140 NaCl, 2.4 KCl, 2 $CaCl_2$), 2 MgCl2, 10 HEPES, 14 Glucose (300 mOsm, pH 7.30)) and TTX (1 µM). Pharmacological reagents (30 µM baclofen, 5 µM CGP), sAPLP1, full length sAPP and sAPP derived peptides (250 nM each) were bath applied (dissolved in external medium described above) using a separate gravity driven application inlet. Recordings were done in whole cell voltage clamp configuration at −70 mV with a double EPC-10 amplifier (HEKA Elektronik) under control of Patchmaster v2×32 software (HEKA Elektronik). Currents were low-pass filtered at 3 kHz and stored at 20 kHz. Patch pipettes were pulled from borosilicate glass using a multi-step puller (P-1000; Sutter Instruments). Pipette resistance ranged from 3 to 5 MΩ and was compensated to 75-80%. Only cells with series resistances <15 MΩ were included in analysis. All recordings were done at room temperature. Spontaneous events were detected using Mini Analysis program (Synaptosoft). mEPSCs and mIPSCs were separated on the basis of their distinct decay kinetics, using a threshold of 5 ms47. Baseline was determined from an average of 60 sec of recordings prior to protein or drug treatment. Effect of treatment was determined from an average of 30 sec recordings after 140 sec of protein or drug treatment.

FM1-43 Dye Labeling

The experiments were performed in mature (15-28 days in vitro) cultures. Hippocampal neurons were imaged using a FV1000 spectral Olympus confocal microscope using a 60×1.2 NA water immersion objective. The experiments were conducted at room temperature in extracellular Tyrode solution containing (in mM): NaCl, 145; KCl, 3; glucose, 15; HEPES, 10; MgCl2, 1.2; $CaCl_2$), 1.2; pH adjusted to 7.4 with NaOH. For FM-based imaging and analysis, activity-dependent FM1-43 (10 µM) styryl dye was used to estimate basal synaptic vesicle recycling using previously described protocol48. Briefly, action potentials were elicited by passing 50 mA constant current for 1 ms through two platinum wires, separated by ~7 mm and close to the surface of the coverslip. The extracellular medium contained non-selective blocker of glutamate receptors (0.5 mM kynurenic acid) to block recurrent neuronal activity. 30 stimuli at 1 Hz were applied during FM1-43 loading, while 800 stimuli at 2 Hz during unloading. The fluorescence of individual synapses was determined from the difference between images obtained after staining and after destining (ΔF). Detection of signals was done using custom-written scripts in MATLAB (Mathworks) as described before48.

Slice Preparation and Electrophysiology

On the day of recording the brain of a 2-month-old Balb/c male mouse was quickly removed and 400 µm-thick horizontal slices were prepared in an ice-cold oxygenated buffer containing (in mM): sucrose, 182; KCl, 2.5; MgSO4, 2; NaH2PO4, 1.25; $NaHCO_3$, 25; $CaCl_2$), 0.8; MgCl2, 5; glucose, 25; ascorbate, 1; HEPES, 20. The slicing procedure was performed using a Leica VT1200 vibrating microtome. Slices were then transferred to a submerged recovery chamber at room temperature containing oxygenated (95% 02 and 5% C02) storage artificial cerebrospinal fluid (ACSF) for 30 min before the incubations (see below). The storage ACSF contained, in mM: NaCl, 100; KCl, 2.5; MgSO4, 2; NaH2PO4, 1.25; $NaHCO_3$, 25; $CaCl_2$), 1.2; MgCl2, 3; glucose, 20; ascorbate, 1; sodium pyruvate,3 and HEPES, 20. The slices were incubated in the incubation chambers perfused with oxygenated storage ACSF containing the experimental agents for 90 min before performing field recordings: In the incubation chamber, control slices were perfused with normal storage ACSF while sAPPα slices were perfused with storage ACSF containing 1 µM sAPPα. CGP slices were perfused with storage ACSF containing 10 µM CGP54626 (Tocris). CGP+sAPPα slices were preincubated in the chamber perfused with ACSF+CGP before being transferred into the chamber perfused with storage ACSF implemented with 10 µM CGP54626+1 µM sAPPα. All recordings were performed at 32-33° C. in a recording chamber perfused with ACSF (4 ml/min) on the stage of an Olympus BX51WI microscope equipped with IR optics and oblique illumination. Recording ACSF contains, in mM: NaCl, 129; KCl, 2.5; $CaCl_2$), 1.2; MgCl2, 1.2; $NaHCO_3$, 25; NaH2PO4, 1.25; glucose, 15. Stimulation of the Schaffer-collateral was delivered through a glass suction electrode (10-20 µm tip) filled with ACSF. fEPSPs were recorded using a glass pipette containing ACSF (1-2 MΩ) from proximal synapses in the CA1 stratum radiatum. Field recording experiments were analyzed using Clampfit.

The invention claimed is:

1. A method of detecting a test compound that modulates the activity of a $GABA_B1a$ receptor, the method comprising:
   a. administering the test compound to a cell expressing a functional $GABA_B1a$ receptor,
   b. detecting binding of the test compound to a sushi domain 1 of the $GABA_B1a$ receptor, and
   detecting a statistically significant change in the activity of the $GABA_B1a$ receptor in the presence of the test compound as compared to the activity of the $GABA_B1a$ receptor in the absence of the test compound.

2. The method according to claim 1, wherein the cell is selected from a recombinant cell, a neuronal cell, and a primary neuron.

3. The method according to claim 2, wherein the primary neuron is present in an acute brain slice obtained from a non-human mammal.

4. The method according to claim 1, wherein the statistically significant change in activity is an increase in the activity of the receptor.

5. The method according to claim 1, wherein the statistically significant change in activity is a reduction in the activity of the receptor.

6. The method according to claim 1, wherein the activity of the $GABA_BR1a$ receptor is detected via calcium release, synaptic transmission, and/or cAMP.

* * * * *

SEQUENCE LISTING

<160> NUMBER OF SEQ ID NOS: 18

<210> SEQ ID NO 1
<211> LENGTH: 33
<212> TYPE: PRT
<213> ORGANISM: Homo sapiens

<400> SEQUENCE: 1

```
Asn Val Asp Ser Ala Asp Ala Glu Glu Asp Asp Ser Asp Val Trp Trp
1               5                   10                  15

Gly Gly Ala Asp Thr Asp Tyr Ala Asp Gly Ser Glu Asp Lys Val Val
            20                  25                  30

Glu

<210> SEQ ID NO 2
<211> LENGTH: 17
<212> TYPE: PRT
<213> ORGANISM: Homo sapiens

<400> SEQUENCE: 2

Asp Asp Ser Asp Val Trp Trp Gly Gly Ala Asp Thr Asp Tyr Ala Asp
1               5                   10                  15

Gly

<210> SEQ ID NO 3
<211> LENGTH: 9
<212> TYPE: PRT
<213> ORGANISM: Homo sapiens

<400> SEQUENCE: 3

Asp Asp Ser Asp Val Trp Trp Gly Gly
1               5

<210> SEQ ID NO 4
<211> LENGTH: 10
<212> TYPE: PRT
<213> ORGANISM: Homo sapiens

<400> SEQUENCE: 4

Gly Gly Ala Asp Thr Asp Tyr Ala Asp Gly
1               5                   10

<210> SEQ ID NO 5
<211> LENGTH: 72
<212> TYPE: PRT
<213> ORGANISM: Homo sapiens

<400> SEQUENCE: 5

Thr Ser Glu Gly Cys Gln Ile Ile His Pro Pro Trp Glu Gly Ile
1               5                   10                  15

Arg Tyr Arg Gly Leu Thr Arg Asp Gln Val Lys Ala Ile Asn Phe Leu
            20                  25                  30

Pro Val Asp Tyr Glu Ile Glu Tyr Val Cys Arg Gly Glu Arg Glu Val
            35                  40                  45

Val Gly Pro Lys Val Arg Lys Cys Leu Ala Asn Gly Ser Trp Thr Asp
        50                  55                  60

Met Asp Thr Pro Ser Arg Cys Val
65                  70

<210> SEQ ID NO 6
<211> LENGTH: 657
<212> TYPE: PRT
<213> ORGANISM: Mus musculus

<400> SEQUENCE: 6

Met Leu Pro Ser Leu Ala Leu Leu Leu Ala Ala Trp Thr Val Arg
1               5                   10                  15

Ala Leu Glu Val Pro Thr Asp Gly Asn Ala Gly Leu Leu Ala Glu Pro
```

```
            20                  25                  30
Gln Ile Ala Met Phe Cys Gly Lys Leu Asn Met His Met Asn Val Gln
            35                  40                  45
Asn Gly Lys Trp Glu Ser Asp Pro Ser Gly Thr Lys Thr Cys Ile Gly
            50                  55                  60
Thr Lys Glu Gly Ile Leu Gln Tyr Cys Gln Glu Val Tyr Pro Glu Leu
65                  70                  75                  80
Gln Ile Thr Asn Val Val Glu Ala Asn Gln Pro Val Thr Ile Gln Asn
                    85                  90                  95
Trp Cys Lys Arg Gly Arg Lys Gln Cys Lys Thr His Thr His Ile Val
                    100                 105                 110
Ile Pro Tyr Arg Cys Leu Val Gly Glu Phe Val Ser Asp Ala Leu Leu
                    115                 120                 125
Val Pro Asp Lys Cys Lys Phe Leu His Gln Glu Arg Met Asp Val Cys
                    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                    165                 170                 175
Asp Lys Phe Arg Gly Val Glu Phe Val Cys Cys Pro Leu Ala Glu Glu
                    180                 185                 190
Ser Asp Ser Val Asp Ser Ala Asp Ala Glu Glu Asp Asp Ser Asp Val
                    195                 200                 205
Trp Trp Gly Gly Ala Asp Thr Asp Tyr Ala Asp Gly Gly Glu Asp Lys
                    210                 215                 220
Val Val Glu Val Ala Glu Glu Glu Val Ala Asp Val Glu Glu Glu
225                 230                 235                 240
Glu Ala Asp Asp Asp Glu Asp Val Glu Asp Gly Asp Glu Val Glu Glu
                    245                 250                 255
Glu Ala Glu Glu Pro Tyr Glu Glu Ala Thr Glu Arg Thr Thr Ser Thr
                    260                 265                 270
Ala Thr Thr Thr Thr Thr Thr Glu Ser Val Glu Glu Val Val Arg
                    275                 280                 285
Val Pro Thr Thr Ala Ala Ser Thr Pro Asp Ala Val Asp Lys Tyr Leu
                    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                    325                 330                 335
Glu Trp Glu Glu Ala Glu Arg Gln Ala Lys Asn Leu Pro Lys Ala Asp
                    340                 345                 350
Lys Lys Ala Val Ile Gln His Phe Gln Glu Lys Val Glu Ser Leu Glu
                    355                 360                 365
Gln Glu Ala Ala Asn Glu Arg Gln Gln Leu Val Glu Thr His Met Ala
                    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro His His Val Phe
                    405                 410                 415
Asn Met Leu Lys Lys Tyr Val Arg Ala Glu Gln Lys Asp Arg Gln His
                    420                 425                 430
Thr Leu Lys His Phe Glu His Val Arg Met Val Asp Pro Lys Lys Ala
                    435                 440                 445
```

-continued

```
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Pro Phe Gly Val Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Gly His Asp Ser Gly Phe Glu Val
        595                 600                 605
Arg His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His

<210> SEQ ID NO 7
<211> LENGTH: 616
<212> TYPE: PRT
<213> ORGANISM: Mus musculus

<400> SEQUENCE: 7

Met Gly Pro Thr Ser Pro Ala Ala Arg Gly Gln Gly Arg Arg Trp Arg
1               5                   10                  15
Pro Pro Leu Pro Leu Leu Leu Pro Leu Ser Leu Leu Leu Leu Arg Ala
                20                  25                  30
Gln Leu Ala Val Gly Asn Leu Ala Val Gly Ser Pro Ser Ala Ala Glu
            35                  40                  45
Ala Pro Gly Ser Ala Gln Val Ala Gly Leu Cys Gly Arg Leu Thr Leu
        50                  55                  60
His Arg Asp Leu Arg Thr Gly Arg Trp Glu Pro Asp Pro Gln Arg Ser
65                  70                  75                  80
Arg Arg Cys Leu Leu Asp Pro Gln Arg Val Leu Glu Tyr Cys Arg Gln
                85                  90                  95
Met Tyr Pro Glu Leu His Ile Ala Arg Val Glu Gln Ala Ala Gln Ala
                100                 105                 110
Ile Pro Met Glu Arg Trp Cys Gly Gly Thr Arg Ser Gly Arg Cys Ala
            115                 120                 125
His Pro His His Glu Val Val Pro Phe His Cys Leu Pro Gly Glu Phe
        130                 135                 140
Val Ser Glu Ala Leu Leu Val Pro Glu Gly Cys Arg Phe Leu His Gln
145                 150                 155                 160
```

```
Glu Arg Met Asp Gln Cys Glu Ser Ser Thr Arg Arg His Gln Glu Ala
                165                 170                 175

Gln Glu Ala Cys Ser Ser Gln Gly Leu Ile Leu His Gly Ser Gly Met
            180                 185                 190

Leu Leu Pro Cys Gly Ser Asp Arg Phe Arg Gly Val Glu Tyr Val Cys
        195                 200                 205

Cys Pro Pro Pro Ala Thr Pro Asn Pro Ser Gly Met Ala Ala Gly Asp
    210                 215                 220

Pro Ser Thr Arg Ser Trp Pro Leu Gly Gly Arg Ala Glu Gly Gly Glu
225                 230                 235                 240

Asp Glu Glu Glu Val Glu Ser Phe Pro Gln Pro Val Asp Asp Tyr Phe
                245                 250                 255

Val Glu Pro Pro Gln Ala Glu Glu Glu Glu Glu Glu Glu Glu Glu Arg
            260                 265                 270

Ala Pro Pro Pro Ser Ser His Thr Pro Val Met Val Ser Arg Val Thr
        275                 280                 285

Pro Thr Pro Arg Pro Thr Asp Gly Val Asp Val Tyr Phe Gly Met Pro
    290                 295                 300

Gly Glu Ile Gly Glu His Glu Gly Phe Leu Arg Ala Lys Met Asp Leu
305                 310                 315                 320

Glu Glu Arg Arg Met Arg Gln Ile Asn Glu Val Met Arg Glu Trp Ala
                325                 330                 335

Met Ala Asp Ser Gln Ser Lys Asn Leu Pro Lys Ala Asp Arg Gln Ala
            340                 345                 350

Leu Asn Glu His Phe Gln Ser Ile Leu Gln Thr Leu Glu Glu Gln Val
        355                 360                 365

Ser Gly Glu Arg Gln Arg Leu Val Glu Thr His Ala Thr Arg Val Ile
    370                 375                 380

Ala Leu Ile Asn Asp Gln Arg Ala Ala Leu Glu Gly Phe Leu Ala
385                 390                 395                 400

Ala Leu Gln Gly Asp Pro Pro Gln Ala Glu Arg Val Leu Met Ala Leu
            405                 410                 415

Arg Arg Tyr Leu Arg Ala Glu Gln Lys Glu Gln Arg His Thr Leu Arg
        420                 425                 430

His Tyr Gln His Val Ala Ala Val Asp Pro Glu Lys Ala Gln Gln Met
    435                 440                 445

Arg Phe Gln Val Gln Thr His Leu Gln Val Ile Glu Glu Arg Met Asn
450                 455                 460

Gln Ser Leu Gly Leu Leu Asp Gln Asn Pro His Leu Ala Gln Glu Leu
465                 470                 475                 480

Arg Pro Gln Ile Gln Glu Leu Leu Ala Glu His Leu Gly Pro Ser
            485                 490                 495

Glu Leu Asp Ala Ser Val Pro Gly Ser Ser Glu Asp Lys Gly Ser
        500                 505                 510

Leu Gln Pro Pro Glu Ser Lys Asp Asp Pro Val Thr Leu Pro Lys
    515                 520                 525

Gly Ser Thr Asp Gln Glu Ser Ser Ser Gly Arg Glu Lys Leu Thr
530                 535                 540

Pro Leu Glu Gln Tyr Glu Gln Lys Val Asn Ala Ser Ala Pro Arg Gly
545                 550                 555                 560

Phe Pro Phe His Ser Ser Asp Ile Gln Arg Asp Glu Leu Ala Pro Ser
                565                 570                 575
```

```
Gly Thr Gly Val Ser Arg Glu Ala Leu Ser Gly Leu Leu Ile Met Gly
            580                 585                 590

Ala Gly Gly Ser Leu Ile Val Leu Ser Leu Leu Leu Arg Lys
        595                 600                 605

Lys Lys Pro Tyr Gly Thr Ile Ser
    610                 615

<210> SEQ ID NO 8
<211> LENGTH: 669
<212> TYPE: PRT
<213> ORGANISM: Mus musculus

<400> SEQUENCE: 8

Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Leu Ala Gly
            20                  25                  30

Tyr Ile Glu Ala Leu Ala Ala Asn Ala Gly Thr Gly Phe Ala Val Ala
            35                  40                  45

Glu Pro Gln Ile Ala Met Phe Cys Gly Lys Leu Asn Met His Val Asn
50                  55                  60

Ile Gln Thr Gly Lys Trp Glu Pro Asp Pro Thr Gly Thr Lys Ser Cys
65                  70                  75                  80

Leu Gly Thr Lys Glu Glu Val Leu Gln Tyr Cys Gln Glu Ile Tyr Pro
                85                  90                  95

Glu Leu Gln Ile Thr Asn Val Met Glu Ala Asn Gln Pro Val Asn Ile
            100                 105                 110

Asp Ser Trp Cys Arg Arg Asp Lys Arg Gln Cys Lys Ser His Ile Val
        115                 120                 125

Ile Pro Phe Lys Cys Leu Val Gly Glu Phe Val Ser Asp Val Leu Leu
130                 135                 140

Val Pro Asp Asn Cys Gln Phe Phe His Gln Glu Arg Met Glu Val Cys
145                 150                 155                 160

Glu Lys His Gln Arg Trp His Thr Leu Val Lys Glu Ala Cys Leu Thr
                165                 170                 175

Glu Gly Leu Thr Leu Tyr Ser Tyr Gly Met Leu Leu Pro Cys Gly Val
            180                 185                 190

Asp Gln Phe His Gly Thr Glu Tyr Val Cys Cys Pro Gln Thr Lys Thr
        195                 200                 205

Val Asp Ser Asp Ser Thr Met Ser Lys Glu Glu Glu Glu Glu
210                 215                 220

Asp Glu Glu Asp Glu Glu Asp Tyr Asp Leu Asp Lys Ser Glu Phe
225                 230                 235                 240

Pro Thr Glu Ala Asp Leu Glu Asp Phe Thr Glu Ala Ala Ala Asp Glu
                245                 250                 255

Glu Glu Glu Asp Glu Glu Glu Gly Glu Val Val Glu Asp Arg Asp
            260                 265                 270

Tyr Tyr Tyr Asp Pro Phe Lys Gly Asp Asp Tyr Asn Glu Glu Asn Pro
        275                 280                 285

Thr Glu Pro Ser Ser Glu Gly Thr Ile Ser Asp Lys Glu Ile Val His
290                 295                 300

Asp Val Lys Val Pro Pro Thr Pro Leu Pro Thr Asn Asp Val Asp Val
305                 310                 315                 320

Tyr Phe Glu Thr Ser Ala Asp Asp Asn Glu His Ala Arg Phe Gln Lys
                325                 330                 335
```

```
Ala Lys Glu Gln Leu Glu Ile Arg His Arg Asn Arg Met Asp Arg Val
            340                 345                 350

Lys Lys Glu Trp Glu Ala Glu Leu Gln Ala Lys Asn Leu Pro Lys
            355                 360                 365

Thr Glu Arg Gln Thr Leu Ile Gln His Phe Gln Ala Met Val Lys Ala
        370                 375                 380

Leu Glu Lys Glu Ala Ala Ser Glu Lys Gln Gln Leu Val Glu Thr His
385                 390                 395                 400

Leu Ala Arg Val Glu Ala Met Leu Asn Asp Arg Arg Ile Ala Leu
                405                 410                 415

Glu Asn Tyr Leu Ala Ala Leu Gln Ser Asp Pro Pro Arg Pro His Arg
            420                 425                 430

Ile Leu Gln Ala Leu Arg Arg Tyr Val Arg Ala Glu Asn Lys Asp Arg
        435                 440                 445

Leu His Thr Ile Arg His Tyr Gln His Val Leu Ala Val Asp Pro Glu
450                 455                 460

Lys Ala Ala Gln Met Lys Ser Gln Val Met Thr His Leu His Val Ile
465                 470                 475                 480

Glu Glu Arg Arg Asn Gln Ser Leu Ser Leu Leu Tyr Lys Val Pro Tyr
                485                 490                 495

Val Ala Gln Glu Ile Gln Glu Val Ile Asp Glu Leu Leu Gln Glu Gln
            500                 505                 510

Arg Ala Asp Met Asp Gln Phe Thr Ser Ser Ile Ser Glu Asn Pro Val
        515                 520                 525

Asp Val Arg Val Ser Ser Glu Glu Ser Glu Glu Ile Pro Pro Phe His
530                 535                 540

Pro Leu His Pro Phe Pro Ser Leu Ser Glu Asn Glu Asp Thr Gln Pro
545                 550                 555                 560

Glu Leu Tyr His Pro Met Lys Lys Gly Ser Gly Met Ala Glu Gln Asp
                565                 570                 575

Gly Gly Leu Ile Gly Ala Glu Glu Lys Val Ile Asn Ser Lys Asn Lys
            580                 585                 590

Met Asp Glu Asn Met Val Ile Asp Glu Thr Leu Asp Val Lys Glu Met
        595                 600                 605

Ile Phe Asn Ala Glu Arg Val Gly Gly Leu Glu Glu Glu Pro Glu Ser
        610                 615                 620

Val Gly Pro Leu Arg Glu Asp Phe Ser Leu Ser Ser Asn Ala Leu Ile
625                 630                 635                 640

Gly Leu Leu Val Ile Ala Val Ala Ile Ala Thr Val Ile Val Ile Ser
                645                 650                 655

Leu Val Met Leu Arg Lys Arg Gln Tyr Gly Thr Ile Ser
            660                 665

<210> SEQ ID NO 9
<211> LENGTH: 36
<212> TYPE: PRT
<213> ORGANISM: Homo sapiens

<400> SEQUENCE: 9

Glu Glu Ser Asp Asn Val Asp Ser Ala Asp Ala Glu Glu Asp Asp Ser
1               5                   10                  15

Asp Val Trp Trp Gly Gly Ala Asp Thr Asp Tyr Ala Asp Gly Ser Glu
            20                  25                  30

Asp Lys Val Val
```

```
                    35

<210> SEQ ID NO 10
<211> LENGTH: 24
<212> TYPE: PRT
<213> ORGANISM: Homo sapiens

<400> SEQUENCE: 10

Gly Thr Pro Asp Pro Ser Gly Thr Ala Val Gly Asp Pro Ser Thr Arg
1               5                   10                  15

Ser Trp Pro Pro Gly Ser Arg Val
            20

<210> SEQ ID NO 11
<211> LENGTH: 32
<212> TYPE: PRT
<213> ORGANISM: Homo sapiens

<400> SEQUENCE: 11

Lys Ile Ile Gly Ser Val Ser Lys Glu Glu Glu Glu Asp Glu Glu
1               5                   10                  15

Glu Glu Glu Glu Glu Asp Glu Glu Asp Tyr Asp Val Tyr Lys Ser
            20                  25                  30

<210> SEQ ID NO 12
<211> LENGTH: 36
<212> TYPE: PRT
<213> ORGANISM: Sus scrofa

<400> SEQUENCE: 12

Glu Glu Ser Asp Asn Ile Asp Ser Ala Asp Ala Glu Glu Asp Ser
1               5                   10                  15

Asp Val Trp Trp Gly Gly Ala Asp Thr Asp Tyr Ala Asp Gly Ser Glu
            20                  25                  30

Asp Lys Val Val
        35

<210> SEQ ID NO 13
<211> LENGTH: 36
<212> TYPE: PRT
<213> ORGANISM: Gallus gallus

<400> SEQUENCE: 13

Glu Glu Ser Asp Asn Leu Asp Ser Ala Asp Ala Glu Asp Asp Ser
1               5                   10                  15

Asp Val Trp Trp Gly Gly Ala Asp Ala Asp Tyr Ala Asp Gly Ser Asp
            20                  25                  30

Asp Lys Val Val
        35

<210> SEQ ID NO 14
<211> LENGTH: 36
<212> TYPE: PRT
<213> ORGANISM: Rattus norvegicus

<400> SEQUENCE: 14

Glu Glu Ser Asp Ser Ile Asp Ser Ala Asp Ala Glu Glu Asp Asp Ser
1               5                   10                  15

Asp Val Trp Trp Gly Gly Ala Asp Thr Asp Tyr Ala Asp Gly Gly Glu
            20                  25                  30

Asp Lys Val Val
```

-continued

```
        35

<210> SEQ ID NO 15
<211> LENGTH: 36
<212> TYPE: PRT
<213> ORGANISM: Mus musculus

<400> SEQUENCE: 15

Glu Glu Ser Asp Ser Val Asp Ser Ala Asp Ala Glu Glu Asp Asp Ser
1               5                   10                  15

Asp Val Trp Trp Gly Gly Ala Asp Thr Asp Tyr Ala Asp Gly Gly Glu
            20                  25                  30

Asp Lys Val Val
        35

<210> SEQ ID NO 16
<211> LENGTH: 35
<212> TYPE: PRT
<213> ORGANISM: Xenopus laevis

<400> SEQUENCE: 16

Glu Glu Ser Glu Ser Phe Asp Ser Ala Asp Ala Glu Asp Asp Ser Asp
1               5                   10                  15

Ala Trp Trp Gly Gly Ala Asp Ala Asp Tyr Val Asp Arg Ser Asp Asp
            20                  25                  30

Lys Ala Val
        35

<210> SEQ ID NO 17
<211> LENGTH: 35
<212> TYPE: PRT
<213> ORGANISM: Danio rerio

<400> SEQUENCE: 17

Ala Gly Lys Glu Ser Glu Ser Ala Ala Val Glu Glu Asp Asp Ser Asp
1               5                   10                  15

Val Trp Trp Gly Gly Ala Glu Ala Asp Tyr Thr Glu Asn Ser Met Thr
            20                  25                  30

Arg Asp Ala
        35

<210> SEQ ID NO 18
<211> LENGTH: 35
<212> TYPE: PRT
<213> ORGANISM: Danio rerio

<400> SEQUENCE: 18

Glu Gln Lys Asp Leu Asp Ser Glu Glu Gln Glu Glu Ala Asn Ser Asp
1               5                   10                  15

Val Trp Trp Gly Gly Ala Glu Thr Glu Tyr Thr Asp Ala Ser Val Leu
            20                  25                  30

Lys Glu Gln
        35
```